United States Patent
Herz et al.

(10) Patent No.: US 10,683,366 B2
(45) Date of Patent: Jun. 16, 2020

(54) METHODS AND COMPOSITIONS FOR TREATMENT OF ATHEROSCLEROSIS

(71) Applicant: BOARD OF REGENTS, THE UNIVERSITY OF TEXAS SYSTEM, Austin, TX (US)

(72) Inventors: Joachim Herz, Austin, TX (US); Yinyuan Ding, Austin, TX (US); Xunde Xian, Austin, TX (US); Linzhang Huang, Austin, TX (US); Chieko Mineo, Austin, TX (US); Philip Shaul, Austin, TX (US); Laurent Calvier, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 15/763,047

(22) PCT Filed: Sep. 23, 2016

(86) PCT No.: PCT/US2016/053351
§ 371 (c)(1),
(2) Date: Mar. 23, 2018

(87) PCT Pub. No.: WO2017/053734
PCT Pub. Date: Mar. 30, 2017

(65) Prior Publication Data
US 2018/0273637 A1 Sep. 27, 2018

Related U.S. Application Data

(60) Provisional application No. 62/233,290, filed on Sep. 25, 2015.

(51) Int. Cl.
| | |
|---|---|
| C07K 16/40 | (2006.01) |
| A61K 45/06 | (2006.01) |
| C12N 15/113 | (2010.01) |
| A01K 67/027 | (2006.01) |
| A61K 38/00 | (2006.01) |
| A61K 31/713 | (2006.01) |
| C07K 16/18 | (2006.01) |
| A61K 39/00 | (2006.01) |
| A61P 9/10 | (2006.01) |

(52) U.S. Cl.
CPC .......... *C07K 16/40* (2013.01); *A01K 67/0276* (2013.01); *A61K 31/713* (2013.01); *A61K 38/00* (2013.01); *A61K 45/06* (2013.01); *C12N 15/1137* (2013.01); *A01K 2217/075* (2013.01); *A01K 2217/15* (2013.01); *A01K 2217/206* (2013.01); *A01K 2227/105* (2013.01); *A01K 2267/0375* (2013.01); *A61K 2039/505* (2013.01); *A61P 9/10* (2018.01); *C07K 16/18* (2013.01); *C07K 2317/21* (2013.01); *C07K 2317/24* (2013.01); *C12N 15/1138* (2013.01); *C12N 2310/14* (2013.01)

(58) Field of Classification Search
None
See application file for complete search history.

(56) References Cited

U.S. PATENT DOCUMENTS 6,323,177 B1 11/2001 Curran et al.
2012/0142544 A1 6/2012 Hare et al.

FOREIGN PATENT DOCUMENTS

WO WO 2014/197752 A1 12/2014

OTHER PUBLICATIONS

D'Arcangelo, et al., Reelin Is a Secreted Glycoprotein Recognized by the CR-50 Monoclonal Antibody, Jan. 1, 1997, The Journal of Neuroscience 17(1):23-31 (Year: 1997).*
Ding et al., Loss of Reelin protects against atherosclerosis by reducing leukocyte-endothelial adhesion and lesion macrophage accumulation, Oct. 6, 2016, Sci Signal. ; 9(419): ra29. doi:10.1126/scisignal.aad5578, 25 pages (Year: 2016).*
Galkina et al., Vascular Adhesion Molecules in Atherosclerosis, 2007, Arterioscler Thomb Vasc Biol. 27:2292-2301 (Year: 2007).*
Baitsch, D., et al., "Apolipoprotein E induces antiinflammatory phenotype in macrophages," *Arteriosclerosis, Thrombosis, and Vascular Biology* 31:1160-1168, 2011.
Beffert, U., et al., "Functional dissection of Reelin signaling by site-directed disruption of Disabled-1 adaptor binding to apolipoprotein E receptor 2: distinct roles in development and synaptic plasticity," *The Journal of Neuroscience* 26:2041-2052, 2006.
Beffert, U., et al., "Reelin-mediated signaling locally regulates protein kinase B/Akt and glycogen synthase kinase 3beta," *The Journal of Biological Chemistry* 277:49958-49964, 2002.
Chen, X., et al., "Up-regulation of ATP binding cassette transporter A1 expression by very low density lipoprotein receptor and apolipoprotein E receptor 2," *The Journal of Biological Chemistry* vol. 287:3751-3759, 2012.
Choi, B.J., et al., "Coronary endothelial dysfunction is associated with inflammation and vasa vasorum proliferation in patients with early atherosclerosis," *Arteriosclerosis, Thrombosis, and Vascular Biology* vol. 34:2473-2477, 2014.
De Bergeyck, V., et al., "A panel of monoclonal antibodies against reelin, the extracellular matrix protein defective in reeler mutant mice," *Journal of Neuroscience Methods* vol. 82:17-24, 1998.
Ding, Y., et al., "Amelioration of hypertriglyceridemia with hypo-alpha-cholesterolemia in LPL deficient mice by hematopoietic cell-derived LPL," *PLoS ONE* vol. 6:e25620, 2011.
Eck, M.V., et al., "Role of the macrophage very-low-density lipoprotein receptor in atherosclerotic lesion development," *Atherosclerosis* 183:230-237, 2005.

(Continued)

*Primary Examiner* — John D Ulm
(74) *Attorney, Agent, or Firm* — Dentons US LLP

(57) ABSTRACT

The present invention provides methods and compositions for treating atherosclerosis in a subject comprising the use of therapeutic compounds to reduce Reelin in the circulation of the subject, thereby reducing the adhesion of leukocytes to the vascular wall. The invention also provides methods and compositions for reducing leukocyte adhesion to the vascular wall in a subject.

15 Claims, 13 Drawing Sheets

Specification includes a Sequence Listing.

(56) References Cited

OTHER PUBLICATIONS

Gaudet, D., et al., "Antisense Inhibition of Apolipoprotein C-III in Patients with Hypertriglyceridemia," *New England Journal of Medicine* 373(5):438-437, 2015.
Graham, M.J., et al., "Antisense oligonucleotide inhibition of apolipoprotein C-III reduces plasma triglycerides in rodents, non-human primates, and humans," *Circulation Res.* 112:1479-1490, 2013.
Hansson, G.K., et al., "The immune response in atherosclerosis: a double-edged sword," *Nature Reviews. Immunology* 6:508-519, 2006.
Hiesberger, T., et al., "Direct binding of Reelin to VLDL receptor and ApoE receptor 2 induces tyrosine phosphorylation of disabled-1 and modulates tau phosphorylation," *Neuron* 24:481-489, 1999.
International Search Report and Written Opinion regarding International Application No. PCT/US2016/053351, dated Jan. 10, 2017.
Knuesel, et al., "Reelin-mediated signaling in neuropsychiatric and neurodegenerative diseases," Progress in Neurobiology, Elsevier, Amsterdam, NL, 91(4):257-274, 2010.
Kubes, P. et al., "Nitric oxide: an endogenous modulator of leukocyte adhesion," *Proceedings of the National Academy of Sciences of the United States of America* 88:4651-4655, 1991.
Lu, H., et al., "Atherosclerosis." *Arteriosclerosis, Thrombosis, and Vascular Biology* 35:485-491, 2015.
May, P., et al., "Molecular mechanisms of lipoprotein receptor signalling," *Cellular and Molecular Life Sciences*, Birkhauser-Verlag, BA, 62(19-20):2325-2338, 2005.
Miao, J., et al., "Role of Insulin in the Regulation of Proprotein Convertase Subtilisin/Kexin type 9," *Arteriosclerosis, Thrombosis, and Vascular Biology* 35(7):1589-96, 2015.
Mudau, M., et al., "Endothelial dysfunction: the early predictor of atherosclerosis," *Cardiovascular Journal of Africa* 23:222-231, 2012.
Okoro, E.U., et al., "A Subregion of Reelin Suppresses Lipoprotein-Induced Cholesterol Accumulation in Macrophages," *PLoS ONE* 10(8):e0136895, 2015.
Ramish, S., et al., "Antiphospholipid antibodies promote leukocyte-endothelial cell adhesion and thrombosis in mice by antagonizing eNOS via beta2GPI and apoER2," *The Journal of Clinical Investigation* 121:120-131, 2011.
Seamus, C.H., et al., "Association of a sequence variant in DAB2IP with coronary heart disease," *European Heart Journal* 33:881-888, 2012.
Smalheiser, N.R., et al., "Expression of reelin in adult mammalian blood, liver, pituitary pars intermedia, and adrenal chromaffin cells," *Proceedings of the National Academy of Sciences of the United States of America*, 97:1281-1286, 2000.
Strickland, D.K. et al., "Diverse roles for the LDL receptor family," *Trends in Endocrinology and Metabolism*, Elsevier Science Publishing, New York, NY, US, 13(2):66-74, 2002.
Tacken, P.J., et al., "VLDL receptor deficiency enhances intimal thickening after vascular injury but does not affect atherosclerotic lesion area," *Atherosclerosis* 162:103-110, 2002.
Tseng, W.L., et al., "Impaired thrombin generation in Reelin-deficient mice: a potential role of plasma Reelin in haemostasis," *Journal of Thrombosis and Haemostasis* 12:2054-2064, 2014.
Tseng, W.L., et al., "Reelin is a platelet protein and functions as a positive regulator of platelet spreading on fibrinogen," *Cellular and Molecular Life Sciences* 67:641-653, 2010.
Tsimikas, S., et al., "Antisense therapy targeting apolipoprotein(a): a randomised double-blind, placebo-controlled phase 1 study," *Lancet* 386(10002)1 472-83, 2015.
Ulrich, V., et al., "Antiphospholipid antibodies attenuate endothelial repair and promote neointima formation in mice," *Journal of the American Heart Association* 3:e001369, 2014.
Ulrich, V., et al., "Genetic variants of ApoE and ApoER2 differentially modulate endothelial function," *Proceedings of the National Academy of Sciences of the United States of America* 111:13493-13498, 2014.
Umetani, M., et al., "The Cholesterol Metabolite 27-Hydroxycholesterol Promotes Atherosclerosis via Proinflammatory Processes Mediated by Estrogen Receptor Alpha," *Cell Metab.* 20:172-82, 2014.
Waltmann, M.D., et al., "Apolipoprotein E receptor-2 deficiency enhances macrophage susceptibility to lipid accumulation and cell death to augment atherosclerotic plaque progression and necrosis," *Biochimica et biophysica acta* 1842:1395-1405, 2014.

* cited by examiner

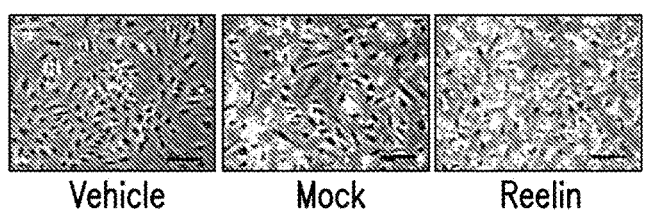
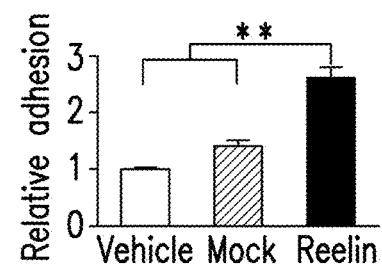
FIG.7A   FIG.7B
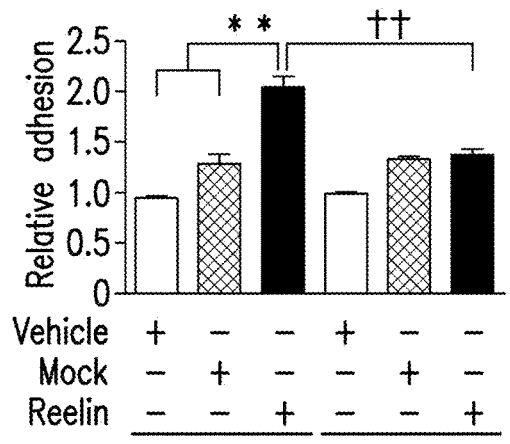
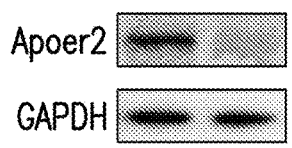
FIG.7C
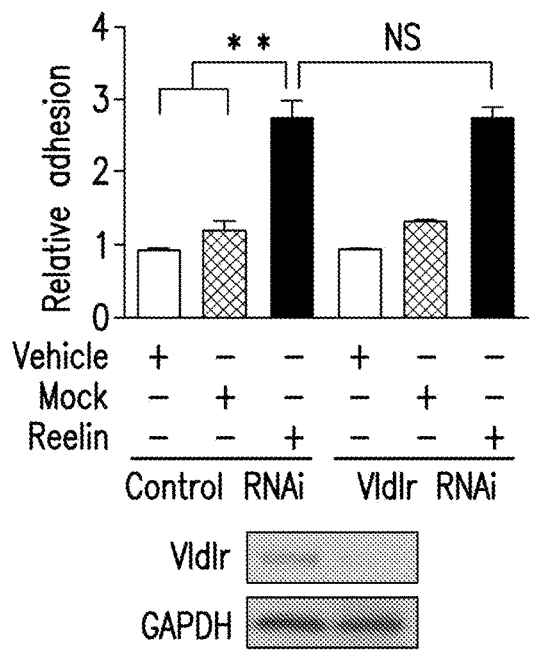
FIG.7D
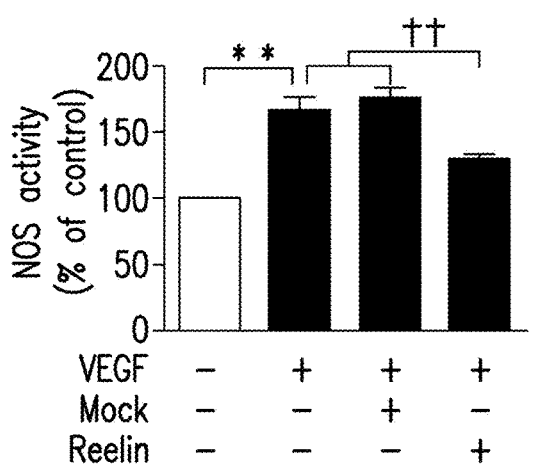
FIG.7E
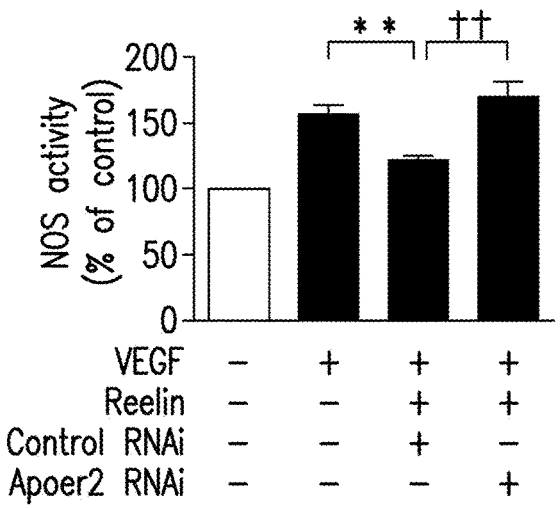
FIG.7F In vivo monocyte adhesion in $CX_3CR1w^{GFP}$ mice In vivo leukocyte adhesion in $CX_3CR1w^{GFP}$ mice

SEQUENCE LISTING

```
<160> NUMBER OF SEQ ID NOS: 5

<210> SEQ ID NO 1
<211> LENGTH: 21
<212> TYPE: DNA
<213> ORGANISM: Homo sapiens

<400> SEQUENCE: 1
gcaguguaau gguauccgat t                                              21

<210> SEQ ID NO 2
<211> LENGTH: 21
<212> TYPE: DNA
<213> ORGANISM: Homo sapiens

<400> SEQUENCE: 2
caucccuaau cuucaccaat t                                              21

<210> SEQ ID NO 3
<211> LENGTH: 11580
<212> TYPE: DNA
<213> ORGANISM: Homo sapiens

<400> SEQUENCE: 3
cacgcgtggg ctcggcgggg gcccgctccc aggcccgctc ccgagcccgt tccgctcccg      60
tccgccttct tctcgccttc tctccgcgtg gctcctccgt cccggcgtct ccaaaactga    120
atgagcgagc ggcgcgtagg gcgscggcgg cggcggcggc ggcggcggcg gcggcatgga    180
gcgcagtggc tgggcccggc agactttcct cctagcgctg ttgctggggg cgacgctgag    240
ggcgcgcgcg gcggctggct attaccccg cttttcgccc ttcttttttcc tgtgcaccca    300 ccacggggag ctggaagggg atgggagca gggcgaggtg ctcatttccc tgcatattgc    360
gggcaacccc acctactacg ttccgggaca agaataccat gtgacaattt caacaagcac    420
```

```
cttttttgac ggcttgctgg tgacaggact atacacatct acaagtgttc aggcatcaca      480
gagcattgga ggttccagtg ctttcggatt tgggatcatg tctgaccacc agtttggtaa      540
ccagtttatg tgcagtgtgg tagcctctca cgtgagtcac ctgcccacaa ccaacctcag      600
tttcatctgg attgctccac ctgcgggcac aggctgtgtg aatttcatgg ctacagcaac      660
acaccggggc caggttattt tcaaagatgc tttagcccag cagttgtgtg aacaaggagc      720
tccaacagat gtcactgtgc acccacatct agctgaaata catagtgaca gcattatcct      780
gagagatgac tttgactcct accaccaact gcaattaaat ccaaatatat gggttgaatg      840
taacaactgt gagactggag aacagtgtgg cgcgattatg catggcaatg ccgtcacctt      900
ctgtgaacca tatggcccac gagaactgat taccacaggc cttaatacaa caacagcttc      960
tgtcctccaa ttttccattg ggtcaggttc atgtcgcttt agttattcag accccagcat     1020
catcgtgtta tatgccaaga ataactctgc ggactggatt cagctagaga aaattagagc     1080
cccttccaat gtcagcacaa tcatccatat cctctacctt cctgaggacg ccaaagggga     1140
gaatgtccaa tttcagtgga agcaggaaaa tcttcgtgta ggtgaagtgt atgaagcctg     1200
ctgggcctta gataacatct tgatcatcaa ttcagctcac agacaagtcg ttttagaaga     1260
tagtctcgac ccagtggaca caggcaactg cttttcttc ccaggagcta cagttaagca     1320
tagctgtcag tcagatggga actccatta ttttccatgga aatgaaggca gcgagttcaa     1380
ttttgccacc accagggatg tagatctttc cacagaagat attcaagagc aatggtcaga     1440
agaatttgag agccagccta caggatggga tgtcttggga gctgtcattg gtacagaatg     1500
tggaacgata gaatcaggct tatcaatggt cttcctcaaa gatggagaga ggaaattatg     1560
cactccatcc atggacacta ccggttatgg gaacctgagg ttttactttg tgatgggagg     1620
aatttgtgac cctggaaatt ctcatgaaaa tgacataatc ctgtatgcaa aaattgaagg     1680
aagaaaagag catataacac tggatacccct ttcctattcc tcatataagg ttccgtctt     1740 ggtttctgtg gtcatcaatc ctgaacttca gactcctgct accaaatttt gtctcaggca     1800
aaagaaccat caaggacata ataggaatgt ctgggctgta gactttttcc atgtcttgcc     1860
tgttctccct tctacaatgt ctcacatgat acagttttcc atcaatctgg gatgtggaac     1920
gcatcagcct ggtaacagtg tcagcttgga attttctacc aaccatgggc gctcctggtc     1980
cctccttcac actgaatgct tacctgagat ctgtgctgga ccccacctcc cccacagcac     2040
tgtctactcc tctgaaaact acagtgggtg gaaccgaata acaattcccc ttcctaacgc     2100
agcactaacc cggaacacca ggattcgctg gagacaaaca ggaccaatcc ttggaaacat     2160
gtgggcaatt gataatgttt atattggccc gtcatgtctc aaattctgtt ctggcagagg     2220
acagtgcact agacatggtt gcaagtgtga ccctggattt tctggcccag cttgtgagat     2280
ggcatcccag acattcccaa tgttttatttc tgaaagcttt ggcagttcca ggctctcctc     2340
ttaccataac ttttactcta tccgtggtgc tgaagtcagc tttggttgtg gtgtcttggc     2400
cagtggtaag gccctggttt tcaacaaaga agggcggcgt cagctaatta catctttcct     2460
tgacagctca caatccaggt ttctccagtt cacactgaga ctggggagca aatctgttct     2520
gagcacgtgc agagcccctg atcagcctgg tgaaggagtt ttgctgcatt attcttatga     2580
taatgggata acttggaaac tcctggagca ttattcatat ctcagctatc atgagcccag     2640
aataatctcc gtagaactac caggtgatgc aaagcagttt ggaattcagt tcagatggtg     2700
gcaaccgtat cattcttccc agagagaaga tgtatgggct attgatgaga ttatcatgac     2760
```

```
atctgtgctt ttcaacagca ttagtcttga cttttaccaat cttgtggagg tcactcagtc   2820
tctgggattc taccttggaa atgttcagcc atactgtggc cacgactgga ccctttgttt   2880
tacaggagat tctaaacttg cctcaagtat gcgctatgtg aaacacaat caatgcagat   2940 aggagcatcc tatatgattc agttcagttt ggtgatggga tgtggccaga aatacacccc   3000
acacatggac aaccaggtga agctggagta ctcaaccaac cacggcctta cctggcacct   3060
cgtccaagaa gaatgccttc caagtatgcc aagttgtcag gaatttacat cagcaagtat   3120
ttaccatgcc agtgagttta cacagtggag gagagtcata gtgcttcttc cccagaaaac   3180
ttggtccagt gctacccgtt ccgctggag ccagagctat tacacagctc aagacgagtg   3240
ggctttggac agcatttaca ttgggcagca gtgccccaac atgtgcagtg gcatggctc   3300 atgcgatcat ggcatatgca ggtgtgacca ggggtaccaa ggcactgaat gccacccaga   3360
agctgccctt ccgtccacaa ttatgtcaga ttttgagaac cagaatggct gggagtctga   3420
ctggcaagaa gttattgggg gagaaattgt aaaaccagaa caagggtgtg gtgtcatctc   3480
ttctggatca tctctgtact tcagcaaggc tgggaaaaga cagctggtga gttgggacct   3540
ggatacttct tgggtggact tgtccagtt ctacatccag ataggcggag agagtgcttc   3600
atgcaacaag cctgacagca gagaggaggg cgtcctcctt cagtacagca acaatgggggg   3660 catccagtgg cacctgctag cagagatgta cttttcagac ttcagcaaac ccagatttgt   3720
ctatctggag cttccagctg ctgccaagac cccttgcacc aggttccgct ggtggcagcc   3780
cgtgttctca ggggaggact atgaccagtg ggcagtcgat gacatcatca ttctgtccga   3840
gaagcagaag cagatcatcc cagttatcaa tccaacttta cctcagaact ttatgagaa   3900 gccagctttt gattacccta tgaatcagat gagtgtgtgg ttgatgttgg ctaatgaagg   3960
aatggttaaa aatgaaacct tctgtgctgc cacaccatca gcaatgatat ttggaaaatc   4020
agatggagat cgatttgcag taactcgaga tttgaccctg aaacctggat atgtgctaca   4080
gttcaagcta aacataggtt gtgccaatca attcagcagt actgctccag ttcttcttca   4140
gtactctcat gatgctggta tgtcctggtt tctggtgaaa aaggctgtt acccggcttc   4200 tgcaggcaaa ggatgcgaag gaaactccag agaactaagt gagcccacca tgtatcacac   4260
aggggacttt gaagaatgga caagaatcac cattgttatt ccaaggtctc ttgcatccag   4320
caagaccaga ttccgatgga tccaggagag cagctcacag aaaaacgtgc ctccatttgg   4380
tttagatgga gtgtacatat ccgagccttg tcccagttac tgcagtggcc atggggactg   4440
catttcagga gtgtgtttct gtgacctggg atatactgct gcacaaggaa cctgtgtgtc   4500
aaatgtcccc aatcacaatg agatgttcga taggtttgag gggaagctca gccctctgtg   4560
gtacaagata acaggtgccc aggttggaac tggctgtgga acacttaacg atggcaaatc   4620
tctctacttc aatggccctg ggaaaaggga agcccggacg gtccctctgg acaccaggaa   4680
tatcagactt gttcaatttt atatacaaat tggaagcaaa acttcaggca ttacctgcat   4740
caaaccaaga actagaaatg aagggcttat tgttcagtat tcaaatgaca atgggatact   4800
ctggcatttg cttcgagagt tggacttcat gtccttcctg gaaccacaga tcatttccat   4860
tgacctgcca caggacgcga agacacctgc aacggcattt cgatggtggc aaccgcaaca   4920
tgggaagcat tcagcccagt gggctttgga tgatgttctt ataggaatga atgacagctc   4980
tcaaactgga tttcaagaca aatttgatgg ctctatagat ttgcaagcca actggtatcg   5040
aatccaagga ggtcaagttg atattgactg tctctctatg gatactgctc tgatattcac   5100
tgaaaacata ggaaaacctc gttatgctga gacctgggat tttcatgtgt cagcatctac   5160
```

```
cttttttgcag tttgaaatga gcatgggctg tagcaagccc ttcagcaact cccacagtgt   5220
acagctccag tattctctga acaatggcaa ggactggcat cttgtcaccg aagagtgtgt   5280
tcctccaacc attggctgtc tgcattacac ggaaagttca atttacacct cggaaagatt   5340
ccagaattgg aagcggatca ctgtctacct tccactctcc accatttctc ccaggacccg   5400
gttcagatgg attcaggcca actacactgt ggggctgat tcctgggcga ttgataatgt    5460
tgtactggcc tcagggtgcc cttggatgtg ctcaggacga gggatttgtg atgctggacg   5520
ctgtgtgtgt gaccggggct ttggtggacc ctattgtgtt cctgttgttc ctctgccctc   5580
gattcttaaa gacgatttca atgggaattt acatcctgac ctttggcctg aagtgtatgg   5640
tgcagagagg gggaatctga atggtgaaac catcaaatct ggaacatctc taattttta   5700
aggggaagga ctaaggatgc ttatttcaag agatctagat tgtacaaata caatgtatgt   5760
ccagttttca cttagattta tagcaaaaag taccccagag agatctcact ctattctgtt   5820
acaattctcc atcagtggag gaatcacttg gcacctgatg gatgaatttt actttcctca   5880
aacaacgaat atacttttca tcaatgttcc cttgccatac actgcccaaa ccaatgctac   5940
aagattcaga ctctggcaac cttataataa cggtaagaaa gaagaaatct ggattgttga   6000
tgacttcatt atcgatggaa ataatgtaaa caaccctgtg atgctcttgg atacatttga   6060
ttttgggccc agagaagaca attggttttt ctatcctggt ggtaacatcg gtctttattg   6120
tccatattct tcaaaggggg cacctgaaga agattcagct atggtgtttg tttcaaatga   6180
agttggtgag cattccatta ccacccgtga cctaaatgtg aatgagaaca ccatcataca   6240
atttgagatc aacgttggct gttcgactga tagctcatcc gcggatccag tgagactgga   6300
atttcaagg gacttcgggg cgacctggca ccttctgctg cccctctgct accacagcag   6360
cagccacgtc agctctttat gctccaccga gcaccacccc agcagcacct actacgcagg   6420
aaccatgcag ggctggagga gggaggtcgt gcactttggg aagctgcacc tttgtggatc   6480
tgtccgtttc agatggtacc agggatttta ccctgccggc tctcagccag tgacatgggc   6540
cattgataat gtctacatcg gtccccagtg tgaggagatg tgtaatggac aggggagctg   6600
tatcaatgga accaaatgta tatgtgaccc tggctactca ggtccaacct gtaaaataag   6660
caccaaaaat cctgattttc tcaaagatga tttcgaaggt cagctagaat ctgatagatt   6720
cttattaatg agtggtggga accatctcg aaagtgtgga atcctttcta gtggaaacaa   6780
cctcttttttc aatgaagatg gcttgcgcat gttgatgaca cgagacctgg attttatcaca   6840
tgctagattt gtgcagttct tcatgagact gggatgtggt aaaggcgttc ctgaccccag   6900
gagtcaaccc gtgctcctac agtattctct caacggtggc ctctcgtgga gtcttcttca   6960
ggagttcctt ttcagcaatt ccagcaatgt gggcaggtac attgccctgg agatacccctt   7020
gaaagcccgt tctggttcta ctcgccttcg ctggtggcaa ccgtctgaga tgggcactt   7080
ctacagcccc tgggttatcg atcagattct tattggagga aatatttctg gtaatacggt   7140
cttggaagat gatttcacaa cccttgatag taggaaatgg ctgcttcacc caggaggcac   7200
caagatgccc gtgtgtggct ctactggtga tgccctggtc ttcattgaaa aggccagcac   7260
ccgttacgtg gtcagcacag acgttgccgt gaatgaggat tccttcctac agatagactt   7320
cgctgcctcc tgctcagtca cagactcttg ttatgcgatt gaattggaat actcagtaga   7380
tcttggattg tcatggcacc cattggtaag ggactgtctg cctaccaatg tggaatgcag   7440
tcgctatcat ctgcaacgga tcctggtgtc agacactttc aacaagtgga ctagaatcac   7500
```

```
tctgcctctc cctccttata ccaggtccca agccactcgt ttccgttggc atcaaccagc    7560
tccttttgac aagcagcaga catgggcaat agataatgtc tatatcgggg atggctgcat    7620
agacatgtgc agtggccatg ggagatgcat ccagggaaac tgcgtctgtg atgaacagtg    7680
gggtggcctg tactgtgatg accccgagac ctctcttcca acccaactca aagacaactt    7740
caatcgagct ccatccagtc agaactggct gactgtgaac ggagggaaat tgagtacagt    7800
gtgtggagcc gtggcgtcgg gaatggctct ccatttcagt gggggttgta gtcgattatt    7860
agtcactgtg gatctaaacc tcactaatgc tgagttcatc caattttact tcatgtatgg    7920
gtgcctgatt acaccaaaca accgtaacca aggtgttctc ttggaatatt ctgtcaatgg    7980
aggcattacc tggaacctgc tcatggagat tttctatgac cagtacagta agcccggatt    8040
tgtgaatatc cttctccctc ctgatgctaa agagattgcc actcgcttcc gctggtggca    8100
gccaagacat gacggcctgg atcagaacga ctgggccatt gacaatgtcc tcatctcagg    8160
ctctgctgac caaaggaccg ttatgctgga caccttcagc agcgcccag tacccagca     8220 cgagcgctcc cctgcagatg ccggcccgt cggaggatc gcctttgaca tgtttatgga     8280
agacaaaact tcagtgaatg agcactggct attccatgat gattgtacag tagaaagatt    8340
ctgtgactcc cctgatggtg tgatgctctg tggcagtcat gatggacggg aggtgtatgc    8400
agtgacccat gacctgactc ccactgaagg ctggattatg caattcaaga tctcagttgg    8460
atgtaaggtg tctgaaaaaa ttgcccagaa tcaaattcat gtgcagtatt ctactgactt    8520
cggtgtgagt tggaattatc tggtccctca gtgcttgcct gctgacccaa aatgctctgg    8580
aagtgtttct cagccatctg tattctttcc aactaagggg tggaaagga tcacctaccc    8640 acttcctgaa agcttagtgg gaaatccggt aaggtttagg ttctatcaga agtactcaga    8700
catgcagtgg gcaatcgata atttctacct gggccctgga tgcttggaca actgcagggg    8760
ccatggagat tgcttaaggg aacagtgcat ctgtgatccg ggatactcag gccaaactg    8820 ctacttgacc cacactctga agactttcct gaaggaacgc tttgacagtg aagaaatcaa    8880
acctgactta tggatgtcct tagaaggtgg aagtacttgc actgagtgtg gaattcttgc    8940
cgaggacact gcactctatt tgggggatc cactgtgaga caagcggtta cacaagattt    9000
ggatcttcga ggtgcaaagt tcctgcaata ctggggcgc atcggtagtg agaacaacat    9060
gacctcttgc catcgtccca tctgccggaa ggaaggcgtg ctgttggact actctaccga    9120
tggaggaatt acctggactt tgctccatga gatggattac cagaaataca tttctgttag    9180
acacgactac atacttcttc ctgaagatgc cctcaccaac acaactcgac ttcgctggtg    9240
gcagcctttt gtgatcagca atggaattgt ggtctctggg gtggagcgtg ctcagtgggc    9300
actggacaac attttgattg gtggagcaga aatcaatccc agccaattgg tggacacttt    9360
tgatgatgaa ggcacttccc atgaagaaaa ctggagtttt taccctaatg ctgtaaggac    9420
agcaggattt tgtggcaatc catcctttca cctctattgg ccaaataaaa agaaggacaa    9480
gactcacaat gctctctcct cccgagaact cattatacag ccaggataca tgatgcagtt    9540
taaaattgtg gtgggttgtg aagccacttc ttgtggtgac cttcattccg taatgctgga    9600
atacactaag gatgcaagat cggattcctg gcagctcgta cagacccagt gccttccttc    9660
ctcttctaac agcattggct gctcccttt ccagttccat gaagccacca tctacaactc    9720
tgtcaacagc tcaagctgga aaagaatcac catccagctg cctgaccatg tctcctctag    9780
tgcaacacag ttccgctgga tccagaaggg agaagaaact gagaagcaaa gctgggcaat    9840
tgaccacgtg tacattggag aggcttgccc caagctctgc agcgggcacg gatactgcac    9900
```

| | |
|---|---|
| gaccggtgcc atctgcatct gcgacgagag cttccaaggt gatgactgct ctgttttcag | 9960 |
| tcacgacctt cccagttata ttaaagataa ttttgagtcc gcaagagtca ccgaggcaaa | 10020 |
| ctgggagacc attcaaggtg gagtcatagg aagtggctgt gggcagctgg cccctacgc | 10080 |
| ccatggagac tcactgtact ttaatggctg tcagatcagg caagcagcta ccaagcctct | 10140 |
| ggatctcact cgagcaagca aaatcatgtt tgttttgcaa attgggagca tgtcgcagac | 10200 |
| ggacagctgc aacagtgacc tgagtggccc ccacgctgtg acaaggcgg tgctgctgca | 10260 |
| atacagcgtc aacaacggga tcacctggca tgtcatcgcc cagcaccagc caaaggactt | 10320 |
| cacacaagct cagagagtgt cttacaatgt ccccctggag gcacggatga aaggagtctt | 10380 |
| actgcgctgg tggcaaccac gccacaatgg aacaggtcat gatcaatggg ctttggacca | 10440 |
| tgtggaggtc gtcctagtaa gcactcgcaa acaaaattac atgatgaatt tttcacgaca | 10500 |
| acatgggctc agacatttct acaacagaag acgaaggtca cttaggcgat acccatgaag | 10560 |
| aatcaaaaag tttatttttt ttcttccaac atgtgatgtg ttgctctcca ttcttttaaa | 10620 |
| tctcgcacta catctgatat caggaaatat ctgtgaagga cttggtgatt acctgaaagc | 10680 |
| ccttctcaag accgagtgta caccactttc ccacactgtg aactaatgac aagtgactta | 10740 |
| tttgctcata agtaaatgtc ttcatgttga tgtgtccgtg aaagttgtga tctgttgtaa | 10800 |
| tatcagttac agtggcagta ttgacaataa gaaacagttt aacagaaaaa tgaaatttaa | 10860 |
| gcacaaaaaa tttaagagat tttatgttta aaatggcatt tagcacagta tttaacattc | 10920 |
| ttggtcacaa agctatttaa gtggactgta tttcagctat gtctcatgtt ttatatgatt | 10980 |
| aaattatcat tgtttgtcct ttatgtattc tcttctacaa tacaacacat tgaaactgta | 11040 |
| tttacttgtt atgttgtaat attttgctgc tgaatttggg gctacttata ttctgcagaa | 11100 |
| aattaattga aatacctatt caagaagata gttgtaaaga tattgtatct cctttaatat | 11160 |
| actccttaaa aatgtatgtt ggtttagcgt tgttttgtgg ataagaaaaa tgcttgaccc | 11220 |
| tgaaatattt tctactttaa attgtggatg aagacccctat ctcccacaaa taagttccca | 11280 |
| tttccttgtc taaagatctt ttttttaagtg ttctgtggct gatttactaa cagtaactgc | 11340 |
| catttttgt ctgtgataac agagtgattt gtaaaacagt ggttgttttt tcattgtgtt | 11400 |
| ttcttcgtgg attgtttttt ctgcgggtca tattcatacc ttctgatgaa gttgtacaac | 11460 |
| accagcaaca ttataatggc cctgtagctc tgaatgctat ttgtgtaact gaaaggttgc | 11520 |
| actctagggt gaaccaagct ataaagccc atgcttaaat aaaaattatg tccaaaagcc | 11580 |

<210> SEQ ID NO 4
<211> LENGTH: 11571
<212> TYPE: DNA
<213> ORGANISM: Homo sapiens

<400> SEQUENCE: 4

| | |
|---|---|
| ctcggcgggg gcccgctccc aggcccgctc ccgagcccgt tccgctcccg tccgccttct | 60 |
| tctcgccttc tctccgcgtg gctcctccgt cccggcgtct ccaaaactga atgagcgagc | 120 |
| ggcgcgtagg gcgcgcggcg gcggcggcgg cggcggcggc atggagcgca gtggctgggc | 180 |
| ccggcagact ttcctcctag cgctgttgct ggggcgacg ctgagggcgc gcgcggcggc | 240 |
| tggctattac ccccgctttt cgcccttctt tttcctgtgc acccaccacg gggagctgga | 300 |
| aggggatggg gagcagggcg aggtgctcat ttccctgcat attgcgggca accccaccta | 360 |
| ctacgttccg ggacaagaat accatgtgac aatttcaaca agcacctttt ttgacggctt | 420 |

```
gctggtgaca ggactataca catctacaag tgttcaggca tcacagagca ttggaggttc    480
cagtgctttc ggatttggga tcatgtctga ccaccagttt ggtaaccagt ttatgtgcag    540
tgtggtagcc tctcacgtga gtcacctgcc cacaaccaac ctcagtttca tctggattgc    600
tccacctgcg ggcacaggct gtgtgaattt catggctaca gcaacacacc ggggccaggt    660
tattttcaaa gatgctttag cccagcagtt gtgtgaacaa ggagctccaa cagatgtcac    720
tgtgcaccca catctagctg aaatacatag tgacagcatt atcctgagag atgactttga    780
ctcctaccac caactgcaat aaatccaaa tatatgggtt gaatgtaaca actgtgagac     840
tggagaacag tgtggcgcga ttatgcatgg caatgccgtc accttctgtg aaccatatgg    900
cccacgagaa ctgattacca caggccttaa tacaacaaca gcttctgtcc tccaattttc    960
cattgggtca ggttcatgtc gctttagtta ttcagacccc agcatcatcg tgttatatgc   1020
caagaataac tctgcggact ggattcagct agagaaaatt gagcccctt ccaatgtcag   1080
cacaatcatc catatcctct accttcctga ggacgccaaa ggggagaatg tccaatttca   1140
gtggaagcag gaaaatcttc gtgtaggtga agtgtatgaa gcctgctggg ccttagataa   1200
catcttgatc atcaattcag ctcacagaca agtcgtttta aagatagtc tcgacccagt    1260
ggacacaggc aactggcttt tcttcccagg agctacagtt aagcatagct gtcagtcaga   1320
tgggaactcc atttatttcc atggaaatga aggcagcgag ttcaattttg ccaccaccag   1380
ggatgtagat cttteccacag aagatattca agagcaatgg tcagaagaat ttgagagcca   1440
gcctacagga tgggatgtct tgggagctgt cattggtaca gaatgtggaa cgatagaatc   1500
aggcttatca atggtcttcc tcaaagatgg agagaggaaa ttatgcactc catccatgga   1560
cactaccggt tatgggaacc tgaggtttta ctttgtgatg ggaggaattt gtgaccctgg   1620
aaattctcat gaaaatgaca atcctgta tgcaaaaatt gaaggaagaa aagagcatat     1680
aacactggat accctttcct attcctcata taaggttccg tctttggttt ctgtggtcat    1740
caatcctgaa cttcagactc ctgctaccaa attttgtctc aggcaaaaga accatcaagg   1800
acataatagg aatgtctggg ctgtagactt tttccatgtc ttgcctgttc tcccttctac   1860
aatgtctcac atgatacagt tttccatcaa tctgggatgt ggaacgcatc agcctggtaa   1920
cagtgtcagc ttggaatttt ctaccaacca tgggcgctcc tggtccctcc ttcacactga   1980
atgcttacct gagatctgtg ctggaccccca cctccccac agcactgtct actcctctga   2040
aaactacagt gggtggaacc gaataacaat tccccttcct aacgcagcac taacccggaa   2100
caccaggatt cgctggagac aaacaggacc aatccttgga acatgtggg caattgataa    2160
tgtttatatt ggcccgtcat gtctcaaatt ctgttctggc agaggacagt gcactagaca   2220
tggttgcaag tgtgaccctg gattttctgg cccagcttgt gagatggcat cccagacatt   2280
cccaatgttt atttctgaaa gctttggcag ttccaggctc tcctcttacc ataactttta   2340
ctctatccgt ggtgctgaag tcagctttgg tgtggtgtc ttggccagtg gtaaggccct    2400
ggttttcaac aaagatgggc ggcgtcagct aattacatct ttccttgaca gctcacaatc   2460
caggtttctc cagttcacac tgagactggg gagcaaatct gttctgagca cgtgcagagc   2520
ccctgatcag cctggtgaag gagttttgtt gcattattct tatgataatg gataacttg    2580
gaaactcctg gagcattatt catatctcag ctatcatgag cccagaataa tctccgtaga   2640
actaccaggt gatgcaaagc agtttggaat tcagttcaga tggtggcaac cgtatcattc   2700
ttcccagaga gaagatgtat gggctattga tgagattatc atgacatctg tgcttttcaa   2760
cagcattagt cttgactta ccaatcttgt ggaggtcact cagtctctgg gattctacct    2820
```

```
tggaaatgtt cagccatact gtggccacga ctggacccttt tgttttacag gagattctaa    2880
acttgcctca agtatgcgct atgtggaaac acaatcaatg cagataggag catcctatat    2940
gattcagttc agtttggtga tgggatgtgg ccagaaatac accccacaca tggacaacca    3000
ggtgaagctg gagtactcaa ccaaccacgg ccttacctgg cacctcgtcc aagaagaatg    3060
ccttccaagt atgccaagtt gtcaggaatt tacatcagca agtatttacc atgccagtga    3120
gtttacacag tggaggagag tcatagtgct tcttccccag aaaacttggt ccagtgctac    3180
ccgtttccgc tggagccaga gctattacac agctcaagac gagtgggctt tggacagcat    3240
ttacattggg cagcagtgcc ccaacatgtg cagtgggcat ggctcatgcg atcatggcat    3300
atgcaggtgt gaccaggggt accaaggcac tgaatgccac ccagaagctg cccttccgtc    3360
cacaattatg tcagattttg agaaccagaa tggctgggag tctgactggc aagaagttat    3420
tgggggagaa attgtaaaac cagaacaagg gtgtggtgtc atctcttctg gatcatctct    3480
gtacttcagc aaggctggga aaagacagct ggtgagttgg gacctggata cttcttgggt    3540
ggactttgtc cagttctaca tccagatagg cggagagagt gcttcatgca acaagcctga    3600
cagcagagag gagggcgtcc tccttcagta cagcaacaat gggggcatcc agtggcacct    3660
gctagcagag atgtactttt cagacttcag caaacccaga tttgtctatc tggagcttcc    3720
agctgctgcc aagacccctt gcaccaggtt ccgctggtgg cagcccgtgt tctcagggga    3780
ggactatgac cagtgggcag tcgatgacat catcattctg tccgagaagc agaagcagat    3840
catcccagtt atcaatccaa ctttacctca gaacttttat gagaagccag cttttgatta    3900
ccctatgaat cagatgagtg tgtggttgat gttggctaat gaaggaatgg ttaaaaatga    3960
aaccttctgt gctgccacac catcagcaat gatatttgga aaatcagatg gagatcgatt    4020
tgcagtaact cgagatttga ccctgaaacc tggatatgtg ctacagttca agctaaacat    4080
aggttgtgcc aatcaattca gcagtactgc tccagttctt cttcagtact ctcatgatgc    4140
tggtatgtcc tggtttctgg tgaaagaagg ctgttacccg gcttctgcag gcaaaggatg    4200
cgaaggaaac tccagagaac taagtgagcc caccatgtat cacacagggg actttgaaga    4260
atggacaaga atcaccattg ttattccaag gtctcttgca tccagcaaga ccagattccg    4320
atggatccag gagagcagct cacagaaaaa cgtgcctcca tttggtttag atggagtgta    4380
catatccgag ccttgtccca gttactgcag tggccatggg gactgcattt caggagtgtg    4440
tttctgtgac ctgggatata ctgctgcaca aggaacctgt gtgtcaaatg tccccaatca    4500
caatgagatg ttcgataggt ttgaggggaa gctcagccct ctgtggtaca agataacagg    4560
tgcccaggtt ggaactggct gtggaacact taacgatggc aaatctctct acttcaatgg    4620
ccctgggaaa agggaagccc ggacggtccc tctggacacc aggaatatca gacttgttca    4680
attttatata caaattggaa gcaaaacttc aggcattacc tgcatcaaac caagaactag    4740
aaatgaaggg cttattgttc agtattcaaa tgacaatggg atactctggc atttgcttcg    4800
agagttggac ttcatgtcct tcctggaacc acagatcatt tccattgacc tgccacagga    4860
cgcgaagaca cctgcaacgg catttcgatg gtggcaaccg caacatggga agcattcagc    4920
ccagtgggct ttggatgatg ttcttatagg aatgaatgac agctctcaaa ctggatttca    4980
agacaaattt gatggctcta tagatttgca agccaactgg tatcgaatcc aaggaggtca    5040
agttgatatt gactgtctct ctatggatac tgctctgata ttcactgaaa acataggaaa    5100
acctcgttat gctgagacct gggattttca tgtgtcagca tctacctttt tgcagtttga    5160
```

```
aatgagcatg ggctgtagca agcccttcag caactcccac agtgtacagc tccagtattc     5220
tctgaacaat ggcaaggact ggcatcttgt caccgaagag tgtgttcctc caaccattgg     5280
ctgtctgcat tacacggaaa gttcaattta cacctcggaa agattccaga attggaagcg     5340
gatcactgtc taccttccac tctccaccat ttctcccagg acccggttca gatggattca     5400
ggccaactac actgtggggg ctgattcctg ggcgattgat aatgttgtac tggcctcagg     5460
gtgcccttgg atgtgctcag gacgagggat ttgtgatgct ggacgctgtg tgtgtgaccg     5520
gggctttggt ggaccctatt gtgttcctgt tgttcctctg ccctcgattc ttaaagacga     5580
tttcaatggg aatttacatc ctgacctttg gcctgaagtg tatggtgcag agaggggaa     5640 tctgaatggt gaaaccatca aatctggaac atctctaatt tttaaagggg aaggactaag     5700
gatgcttatt tcaagagatc tagattgtac aaatacaatg tatgtccagt tttcacttag     5760
atttatagca aaaagtaccc cagagagatc tcactctatt ctgttacaat tctccatcag     5820
tggaggaatc acttggcacc tgatggatga atttttacttt cctcaaacaa cgaatatact     5880
tttcatcaat gttcccttgc catacactgc ccaaaccaat gctacaagat tcagactctg     5940
gcaaccttat aataacggta agaaagaaga aatctggatt gttgatgact tcattatcga     6000
tggaaataat gtaaacaacc ctgtgatgct cttggataca tttgattttg ggcccagaga     6060
agacaattgg ttttctatc ctggtggtaa catcggtctt tatttgtccat attcttcaaa     6120 gggggcacct gaagaagatt cagctatggt gtttgtttca aatgaagttg gtgagcattc     6180
cattaccacc cgtgacctaa atgtgaatga gaacaccatc atacaatttg agatcaacgt     6240
tggctgttcg actgatagct catccgcgga tccagtgaga ctggaatttt caagggactt     6300
cggggcgacc tggcaccttc tgctgcccct ctgctaccac agcagcagcc acgtcagctc     6360
tttatgctcc accgagcacc accccagcag cacctactac gcaggaacca tgcagggctg     6420
gaggagggag gtcgtgcact ttgggaagct gcacctttgt ggatctgtcc gtttcagatg     6480
gtaccaggga ttttaccctg ccggctctca gccagtgaca tgggccattg ataatgtcta     6540
catcggtccc cagtgtgagg agatgtgtaa tggacagggg agctgtatca atggaaccaa     6600
atgtatatgt gaccctggct actcaggtcc aacctgtaaa ataagcacca aaaatcctga     6660
ttttctcaaa gatgatttcg aaggtcagct agaatctgat agattcttat taatgagtgg     6720
tgggaaacca tctcgaaagt gtggaatcct ttcagtgga aacaacctct ttttcaatga     6780
agatggcttg cgcatgttga tgacacgaga cctggattta tcacatgcta gatttgtgca     6840
gttcttcatg agactgggat gtggtaaagg cgttcctgac cccaggagtc aacccgtgct     6900
cctacagtat tctctcaacg gtggcctctc gtggagtctt cttcaggagt tccttttcag     6960
caattccagc aatgtgggca ggtacattgc cctggagata cccttgaaag cccgttctgg     7020
ttctactcgc cttcgctggt ggcaaccgtc tgagaatggg cacttctaca gcccctgggt     7080
tatcgatcag attcttattg gaggaaatat ttctggtaat acggtcttgg aagatgattt     7140
cacaaccctt gatagtagga atggctgctc accccagga ggcaccaaga tgcccgtgtg     7200
tggctctact ggtgatgccc tggtcttcat tgaaaaggcc agcacccgtt acgtggtcag     7260
cacagacgtt gccgtgaatg aggattcctt cctacagata gacttcgctg cctcctgctc     7320
agtcacagac tcttgttatg cgattgaatt ggaatactca gtagatcttg gattgtcatg     7380
gcacccattg gtaagggact gtctgcctac caatgtggaa tgcagtcgct atcatctgca     7440
acggatcctg tgtcagaca cttttcaacaa gtggactaga atcactctgc ctctccctcc     7500
ttataccagg tcccaagcca ctcgtttccg ttggcatcaa ccagctcctt ttgacaagca     7560
```

```
gcagacatgg gcaatagata atgtctatat cggggatggc tgcatagaca tgtgcagtgg    7620
ccatgggaga tgcatccagg gaaactgcgt ctgtgatgaa cagtggggtg gcctgtactg    7680
tgatgacccc gagacctctc ttccaaccca actcaaagac aacttcaatc gagctccatc    7740
cagtcagaac tggctgactg tgaacggagg gaaattgagt acagtgtgtg gagccgtggc    7800
gtcgggaatg gctctccatt tcagtggggg ttgtagtcga ttattagtca ctgtggatct    7860
aaacctcact aatgctgagt tcatccaatt ttacttcatg tatgggtgcc tgattacacc    7920
aaacaaccgt aaccaaggtg ttctcttgga atattctgtc aatggaggca ttacctggaa    7980
cctgctcatg gagattttct atgaccagta cagtaagccc ggatttgtga atatccttct    8040
ccctcctgat gctaaagaga ttgccactcg cttccgctgg tggcagccaa gacatgacgg    8100
cctggatcag aacgactggg ccattgacaa tgtcctcatc tcaggctctg ctgaccaaag    8160
gaccgttatg ctggacacct tcagcagcgc cccagtaccc cagcatgagc gctcccctgc    8220
agatgccggc cctgtcggga ggatcgcctt tgacatgttt atggaagaca aaacttcagt    8280
gaatgagcac tggctattcc atgatgattg tacagtagaa agattctgtg actcccctga    8340
tggtgtgatg ctctgtggca gtcatgatgg acgggaggtg tatgcagtga cccatgacct    8400
gactcccact gaaggctgga ttatgcaatt caagatctca gttggatgta aggtgtctga    8460
aaaaattgcc cagaatcaaa ttcatgtgca gtattctact gacttcggtg tgagttggaa    8520
ttatctggtc cctcagtgct tgcctgctga cccaaaatgc tctggaagtg tttctcagcc    8580
atctgtattc tttccaacta aagggtggaa aaggatcacc tacccacttc ctgaaagctt    8640
agtgggaaat ccggtaaggt ttaggttcta tcagaagtac tcagacatgc agtgggcaat    8700
cgataatttc tacctgggcc ctggatgctt ggacaactgc aggggccatg agattgctt    8760 aagggaacag tgcatctgtg atccgggata ctcagggcca aactgctact tgacccacac    8820
tctgaagact ttcctgaagg aacgctttga cagtgaagaa atcaaacctg acttatggat    8880
gtccttagaa ggtggaagta cttgcactga gtgtggaatt cttgccgagg acactgcact    8940
ctattttggg ggatccactg tgagacaagc ggttacacaa gatttggatc ttcgaggtgc    9000
aaagttcctg caatactggg ggcgcatcgg tagtgagaac aacatgacct cttgccatcg    9060
tcccatctgc cggaaggaag gcgtgctgtt ggactactct accgatggag gaattacctg    9120
gactttgctc catgagatgg attaccagaa atacatttct gttagacacg actacatact    9180
tcttcctgaa gatgccctca ccaacacaac tcgacttcgc tggtggcagc cttttgtgat    9240
cagcaatgga attgtggtct ctggggtgga gcgtgctcag tgggcactgg acaacatttt    9300
gattggtgga gcagaaatca atcccagcca attggtggac acttttgatg atgaaggcac    9360
ttcccatgaa gaaaactgga gttttttaccc taatgctgta aggacagcag attttgtgg    9420 caatccatcc tttcacctct attggccaaa taaaagaag gacaagactc acaatgctct    9480
ctcctcccga gaactcatta tacagccagg atacatgatg cagtttaaaa ttgtggtggg    9540
ttgtgaagcc acttcttgtg gtgaccttca ttccgtaatg ctggaataca ctaaggatgc    9600
aagatcggat tcctggcagc tcgtacagac ccagtgcctt ccttcctctt ctaacagcat    9660
tggctgctcc ccttccagt tccatgaagc caccatctac aactctgtca acagctcaag    9720
ctggaaaaga atcaccatcc agctgcctga ccatgtctcc tctagtgcaa cacagttccg    9780
ctggatccag aagggagaag aaactgagaa gcaaagctgg gcaattgacc acgtgtacat    9840
tggagaggct tgccccaagc tctgcagcgg gcacggatac tgcacgaccg gtgccatctg    9900
```

```
catctgcgac gagagcttcc aaggtgatga ctgctctgtt ttcagtcacg accttcccag      9960
ttatattaaa gataattttg agtccgcaag agtcaccgag gcaaactggg agaccattca     10020
aggtggagtc ataggaagtg gctgtgggca gctggccccc tacgcccatg gagactcact     10080
gtactttaat ggctgtcaga tcaggcaagc agctaccaag cctctggatc tcactcgagc     10140
aagcaaaatc atgtttgttt tgcaaattgg gagcatgtcg cagacggaca gctgcaacag     10200
tgacctgagt ggcccccacg ctgtggacaa ggcagtgctg ctgcaataca gcgtcaacaa     10260
cgggatcacc tggcatgtca tcgcccagca ccagccaaag gacttcacac aagctcagag     10320
agtgtcttac aatgtccccc tggaggcacg gatgaaagga gtcttactgc gctggtggca     10380
accacgccac aatggaacag gtcatgatca atgggctttg gaccatgtgg aggtcgtcct     10440
agtaagcact cgcaaacaaa attacatgat gaatttttca cgacaacatg ggctcagaca     10500
tttctacaac agaagacgaa ggtcacttag gcgataccca tgaagaatca aaaagtttat     10560
tttttttctt ccaacatgtg atgtgttgct ctccattctt ttaaatctcg cactacatct     10620
gatatcagga aatatctgtg aaggacttgg tgattacctg aaagcccttc tcaagaccga     10680
gtgtacacca ctttcccaca ctgtgaacta atgacaagtg acttatttgc tcataagtaa     10740
atgtcttcat gttgatgtgt ccgtgaaagt tgtgatctgt tgtaatatca gttacagtgg     10800
cagtattgac aataagaaac agtttaacag aaaaatgaaa tttaagcaca aaaaatttaa     10860
gagattttat gtttaaaatg gcatttagca cagtatttaa cattcttggt cacaaagcta     10920
tttaagtgga ctgtatttcg gctatgtctc atgtttttata tgattaaatt atcattgttt     10980
gtcctttatg tattctcttc tacaatacaa cacattgaaa ctgtatttac ttgttatgtt     11040
gtaatatttt gctgctgaat ttggggctac ttatattctg cagaaaatta attgaaatac     11100
ctattcaaga agatagttgt aaagatattg tatctccttt aatatactcc ttaaaaatgt     11160
atgttggttt agcgttgttt tgtggataag aaaaatgctt gaccctgaaa tattttctac     11220
tttaaattgt ggatgaagac cctatctccc acaaataagt tcccatttcc ttgtctaaag     11280
atctttttttt aagtgttctg tggctgattt actaacagta actgccatt  tttgtctgtg      11340
ataacagagt gatttgtaaa acagtggttg ttttttcatt gtgttttctt cgtggattgt     11400
tttttctgcg ggtcatattc atacccttctg atgaagttgt acaacaccag caacattata     11460
atggccctgt agctctgaat gctatttgtg taactgaaag gttgcactct agggtgaacc     11520
aagctataaa agcccatgct taaataaaaa ttatgtccaa aagccattga a                11571
```

<210> SEQ ID NO 5
<211> LENGTH: 11565
<212> TYPE: DNA
<213> ORGANISM: Homo sapiens

<400> SEQUENCE: 5

```
ctcggcgggg gcccgctccc aggcccgctc ccgagcccgt tccgctcccg tccgccttct        60
tctcgccttc tctccgcgtg gctcctccgt cccggcgtct ccaaaactga atgagcgagc       120
ggcgcgtagg gcgcgcggcg gcgcggcgg  cggcggcggc atggagcgca gtggctgggc       180
ccggcagact ttcctcctag cgctgttgct ggggcgacg ctgagggcgc gcgcggcggc       240
tggctattac ccccgctttt cgcccttctt tttcctgtgc acccaccacg gggagctgga       300
aggggatggg gagcagggcg aggtgctcat ttccctgcat attgcgggca accccaccta       360
ctacgttccg ggacaagaat accatgtgac aatttcaaca agcaccttt  ttgacgcgtt       420
gctggtgaca ggactataca catctacaag tgttcaggca tcacagagca ttggaggttc       480
```

```
cagtgctttc ggatttggga tcatgtctga ccaccagttt ggtaaccagt ttatgtgcag      540
tgtggtagcc tctcacgtga gtcacctgcc cacaaccaac ctcagtttca tctggattgc      600
tccacctgcg ggcacaggct gtgtgaattt catggctaca gcaacacacc ggggccaggt      660
tattttcaaa gatgctttag cccagcagtt gtgtgaacaa ggagctccaa cagatgtcac      720
tgtgcaccca catctagctg aaatacatag tgacagcatt atcctgagag atgactttga      780
ctcctaccac caactgcaat taaatccaaa tatatgggtt gaatgtaaca actgtgagac      840
tggagaacag tgtggcgcga ttatgcatgg caatgccgtc accttctgtg aaccatatgg      900
cccacgagaa ctgattacca caggccttaa tacaacaaca gcttctgtcc tccaattttc      960
cattgggtca ggttcatgtc gctttagtta ttcagacccc agcatcatcg tgttatatgc     1020
caagaataac tctgcggact ggattcagct agagaaaatt agagcccctt ccaatgtcag     1080
cacaatcatc catatcctct accttcctga ggacgccaaa ggggagaatg tccaatttca     1140
gtggaagcag gaaaatcttc gtgtaggtga agtgtatgaa gcctgctggg ccttagataa     1200
catcttgatc atcaattcag ctcacagaca agtcgtttta aagatagtc tcgacccagt      1260 ggacacaggc aactggcttt tcttcccagg agctacagtt aagcatagct gtcagtcaga     1320
tgggaactcc atttatttcc atggaaatga aggcagcgag ttcaattttg ccaccaccag     1380
ggatgtagat ctttccacag aagatattca agagcaatgg tcagaagaat ttgagagcca     1440
gcctacagga tgggatgtct tgggagctgt cattggtaca gaatgtggaa cgatagaatc     1500
aggcttatca atggtcttcc tcaaagatgg agagaggaaa ttatgcactc catccatgga     1560
cactaccggt tatgggaacc tgaggtttta ctttgtgatg ggaggaattt gtgaccctgg     1620
aaattctcat gaaaatgaca taatcctgta tgcaaaaatt gaaggaagaa aagagcatat     1680
aacactggat acccttttcct attcctcata taaggttccg tctttggttt ctgtggtcat     1740
caatcctgaa cttcagactc ctgctaccaa atttttgtctc aggcaaaaga accatcaagg     1800
acataatagg aatgtctggg ctgtagactt tttccatgtc ttgcctgttc tcccttctac     1860
aatgtctcac atgatacagt tttccatcaa tctgggatgt ggaacgcatc agcctggtaa     1920
cagtgtcagc ttggaatttt ctaccaacca tgggcgctcc tggtccctcc ttcacactga     1980
atgcttacct gagatctgtg ctggaccca cctccccac agcactgtct actcctctga      2040
aaactacagt gggtggaacc gaataacaat tccccttcct aacgcagcac taaccccgaa     2100
caccaggatt cgctggagac aaacaggacc aatccttgga aacatgtggg caattgataa     2160
tgtttatatt ggcccgtcat gtctcaaatt ctgttctggc agaggacagt gcactagaca     2220
tggttgcaag tgtgaccctg attttctgg cccagcttgt gagatggcat cccagacatt     2280
cccaatgttt atttctgaaa gctttggcag ttccaggctc tcctcttacc ataactttta     2340
ctctatccgt ggtgctgaag tcagctttgg ttgtggtgtc ttggccagtg gtaaggccct     2400
ggttttcaac aaagatgggc ggcgtcagct aattacatct ttccttgaca gctcacaatc     2460
caggtttctc cagttcacac tgagactggg gagcaaatct gttctgagca cgtgcagagc     2520
ccctgatcag cctggtgaag gagttttgtt gcattattct tatgataatg gataacttg      2580 gaaactcctg gagcattatt catatctcag ctatcatgag cccagaataa tctccgtaga     2640
actaccaggt gatgcaaagc agtttggaat tcagttcaga tggtggcaac cgtatcattc     2700
ttcccagaga gaagatgtat gggctattga tgagattatc atgacatctg tgcttttcaa     2760
cagcattagt cttgactta ccaatcttgt ggaggtcact cagtctctgg gattctacct       2820
```

```
tggaaatgtt cagccatact gtggccacga ctggacccct tgttttacag gagattctaa    2880
acttgcctca agtatgcgct atgtggaaac acaatcaatg cagataggag catcctatat    2940
gattcagttc agtttggtga tgggatgtgg ccagaaatac accccacaca tggacaacca    3000
ggtgaagctg gagtactcaa ccaaccacgg ccttacctgg cacctcgtcc aagaagaatg    3060
ccttccaagt atgccaagtt gtcaggaatt tacatcagca agtatttacc atgccagtga    3120
gtttacacag tggaggagag tcatagtgct tcttccccag aaaacttggt ccagtgctac    3180
ccgtttccgc tggagccaga gctattacac agctcaagac gagtgggctt tggacagcat    3240
ttacattggg cagcagtgcc ccaacatgtg cagtgggcat ggctcatgcg atcatggcat    3300
atgcaggtgt gaccagaggt accaaggcac tgaatgccac ccagaagctg cccttccgtc    3360
cacaattatg tcagattttg agaaccagaa tggctgggag tctgactggc aagaagttat    3420
tgggggagaa attgtaaaac cagaacaagg gtgtggtgtc atctcttctg gatcatctct    3480
gtacttcagc aaggctggga aagacagct ggtgagttgg gacctggata cttcttgggt    3540
ggactttgtc cagttctaca tccagatagg cggagagagt gcttcatgca acaagcctga    3600
cagcagagag gagggcgtcc tccttcagta cagcaacaat gggggcatcc agtggcacct    3660
gctagcagag atgtactttt cagacttcag caaacccaga tttgtctatc tggagcttcc    3720
agctgctgcc aagacccctt gcaccaggtt ccgctggtgg cagcccgtgt ctcagggga    3780 ggactatgac cagtgggcag tcgatgacat catcattctg tccgagaagc agaagcagat    3840
catcccagtt atcaatccaa ctttacctca gaactttat gagaagccag cttttgatta    3900
ccctatgaat cagatgagtg tgtggttgat gttggctaat gaaggaatgg ttaaaaatga    3960
aaccttctgt gctgccacac catcagcaat gatatttgga aaatcagatg gagatcgatt    4020
tgcagtaact cgagatttga ccctgaaacc tggatatgtg ctacagttca agctaaacat    4080
aggttgtgcc aatcaattca gcagtactgc tccagttctt cttcagtact ctcatgatgc    4140
tggtatgtcc tggtttctgg tgaaagaagg ctgttacccg gcttctgcag gcaaaggatg    4200
cgaaggaaac tccagagaac taagtgagcc caccatgtat cacacagggg actttgaaga    4260
atggacaaga atcaccattg ttattccaag gtctcttgca tccagcaaga ccagattccg    4320
atggatccag gagagcagct cacagaaaaa cgtgcctcca tttggtttag atggagtgta    4380
catatccgag ccttgtccca gttactgcag tggccatggg gactgcattt caggagtgtg    4440
tttctgtgac ctgggatata ctgctgcaca aggaacctgt gtgtcaaatg tccccaatca    4500
caatgagatg ttcgataggt ttgaggggaa gctcagccct ctgtggtaca agataacagg    4560
tgcccaggtt ggaactggct gtggaacact aacgatggc aaatctctct acttcaatgg    4620
ccctgggaaa agggaagccc ggacggtccc tctggacacc aggaatatca gacttgttca    4680
attttatata caaattggaa gcaaaacttc aggcattacc tgcatcaaac caagaactag    4740
aaatgaaggg cttattgttc agtattcaaa tgacaatggg atactctggc atttgcttcg    4800
agagttggac ttcatgtcct tcctggaacc acagatcatt ccattgacc tgccacagga    4860 cgcgaagaca cctgcaacgg catttcgatg gtggcaaccg caacatggga agcattcagc    4920
ccagtgggct ttgatgatg ttcttatagg aatgaatgac agctctcaaa ctggatttca    4980
agacaaattt gatggctcta tagatttgca agccaactgg tatcgaatcc aaggaggtca    5040
agttgatatt gactgtctct ctatggatac tgctctgata ttcactgaaa acataggaaa    5100
acctcgttat gctgagacct gggattttca tgtgtcagca tctacctttt tgcagtttga    5160
aatgagcatg ggctgtagca agcccttcag caactccac agtgtacagc tccagtattc    5220
```

```
tctgaacaat ggcaaggact ggcatcttgt caccgaagag tgtgttcctc caaccattgg   5280
ctgtctgcat tacacggaaa gttcaattta cacctcggaa agattccaga attggaagcg   5340
gatcactgtc taccttccac tctccaccat ttctcccagg acccggttca gatggattca   5400
ggccaactac actgtggggg ctgattcctg ggcgattgat aatgttgtac tggcctcagg   5460
gtgcccttgg atgtgctcag gacgagggat ttgtgatgct ggacgctgtg tgtgtgaccg   5520
gggctttggt ggaccctatt tgttcctgt tgttcctctg ccctcgattc ttaaagacga   5580
tttcaatggg aatttacatc ctgacctttg gcctgaagtg tatggtgcag agaggggaa   5640 tctgaatggt gaaaccatca aatctggaac atctctaatt tttaaagggg aaggactaag   5700
gatgcttatt tcaagagatc tagattgtac aaatacaatg tatgtccagt tttcacttag   5760
atttatagca aaaagtaccc cagagagatc tcactctatt ctgttacaat ctccatcag   5820 tggaggaatc acttggcacc tgatggatga atttttacttt cctcaaacaa cgaatatact   5880
tttcatcaat gttcccttgc catacactgc ccaaaccaat gctacaagat tcagactctg   5940
gcaaccttat aataacggta agaaagaaga atctggatt gttgatgact tcattatcga   6000
tggaaataat gtaaacaacc ctgtgatgct cttggataca tttgattttg ggcccagaga   6060
agacaattgg ttttctatc ctggtggtaa catcggtctt tattgtccat attcttcaaa   6120
gggggcacct gaagaagatt cagctatggt gtttgtttca aatgaagttg gtgagcattc   6180
cattaccacc cgtgacctaa atgtgaatga gaacaccatc atacaatttg agatcaacgt   6240
tggctgttcg actgatagct catccgcgga tccagtgaga ctggaatttt caagggactt   6300
cggggcgacc tggcaccttc tgctgcccct ctgctaccac agcagcagcc acgtcagctc   6360
tttatgctcc accgagcacc accccagcag cacctactac gcaggaacca tgcagggctg   6420
gaggagggag gtcgtgcact tgggaagct gcacctttgt ggatctgtcc gttttcagatg   6480 gtaccaggga ttttaccctg ccggctctca gccagtgaca tgggccattg ataatgtcta   6540
catcggtccc cagtgtgagg agatgtgtaa tggacagggg agctgtatca atggaaccaa   6600
atgtatatgt gaccctggct actcaggtcc aacctgtaaa ataagcacca aaaatcctga   6660
ttttctcaaa gatgatttcg aaggtcagct agaatctgat agattcttat taatgagtgg   6720
tgggaaacca tctcgaaagt gtggaatcct ttctagtgga aacaacctct ttttcaatga   6780
agatggcttg cgcatgttga tgacacgaga cctggattta tcacatgcta gatttgtgca   6840
gttcttcatg agactgggat gtggtaaagg cgttcctgac cccaggagtc aacccgtgct   6900
cctacagtat tctctcaacg gtggcctctc gtggagtctt cttcaggagt tccttttcag   6960
caattccagc aatgtgggca ggtacattgc cctggagata cccttgaaag cccgttctgg   7020
ttctactcgc cttcgctggt ggcaaccgtc tgagaatggg cacttctaca gccctgggt   7080 tatcgatcag attcttattg gaggaaatat ttctggtaat acggtcttgg aagatgattt   7140 cacaacccctt gatagtagga aatggctgct tcacccagga ggcaccaaga tgcccgtgtg   7200
tggctctact ggtgatgccc tggtcttcat tgaaaaggcc agcacccgtt acgtggtcag   7260
cacagacgtt gccgtgaatg aggattcctt cctacagata gacttcgctg cctcctgctc   7320
agtcacagac tcttgttatg cgattgaatt ggaatactca gtagatcttg gattgtcatg   7380
gcacccattg gtaagggact gtctgcctac caatgtggaa tgcagtcgct atcatctgca   7440
acggatcctg gtgtcagaca cttttcaacaa gtggactaga atcactctgc ctctccctcc   7500
ttataccagg tcccaagcca ctcgtttccg ttggcatcaa ccagctcctt ttgacaagca   7560
```

```
gcagacatgg gcaatagata atgtctatat cggggatggc tgcatagaca tgtgcagtgg    7620
ccatgggaga tgcatccagg gaaactgcgt ctgtgatgaa cagtggggtg gcctgtactg    7680
tgatgacccc gagacctctc ttccaaccca actcaaagac aacttcaatc gagctccatc    7740
cagtcagaac tggctgactg tgaacggagg gaaattgagt acagtgtgtg gagccgtggc    7800
gtcgggaatg gctctccatt tcagtggggg ttgtagtcga ttattagtca ctgtggatct    7860
aaacctcact aatgctgagt tcatccaatt ttacttcatg tatgggtgcc tgattacacc    7920
aaacaaccgt aaccaaggtg ttctcttgga atattctgtc aatggaggca ttacctggaa    7980
cctgctcatg gagattttct atgaccagta cagtaagccc ggatttgtga atatccttct    8040
ccctcctgat gctaaagaga ttgccactcg cttccgctgg tggcagccaa gacatgacgg    8100
cctggatcag aacgactggg ccattgacaa tgtcctcatc tcaggctctg ctgaccaaag    8160
gaccgttatg ctggacacct tcagcagcgc cccagtaccc cagcatgagc gctcccctgc    8220
agatgccggc cctgtcggga ggatcgcctt tgacatgttt atggaagaca aaacttcagt    8280
gaatgagcac tggctattcc atgatgattg tacagtagaa agattctgtg actcccctga    8340
tggtgtgatg ctctgtggca gtcatgatgg acgggaggtg tatgcagtga cccatgacct    8400
gactcccact gaaggctgga ttatgcaatt caagatctca gttggatgta aggtgtctga    8460
aaaaattgcc cagaatcaaa ttcatgtgca gtattctact gacttcggtg tgagttggaa    8520
ttatctggtc cctcagtgct tgcctgctga cccaaaatgc tctggaagtg tttctcagcc    8580
atctgtattc tttccaacta aagggtggaa aaggatcacc tacccacttc ctgaaagctt    8640
agtgggaaat ccgtaaggt ttaggttcta tcagaagtac tcagacatgc agtgggcaat    8700
cgataatttc tacctgggcc ctggatgctt ggacaactgc aggggccatg gagattgctt    8760
aagggaacag tgcatctgtg atccgggata ctcagggcca aactgctact tgacccacac    8820
tctgaagact ttcctgaagg aacgctttga cagtgaagaa atcaaacctg acttatggat    8880
gtccttagaa ggtggaagta cttgcactga gtgtggaatt cttgccgagg acactgcact    8940
ctattttggg ggatccactg tgagacaagc ggttacacaa gatttggatc ttcgaggtgc    9000
aaagttcctg caatactggg ggcgcatcgg tagtgagaac aacatgacct cttgccatcg    9060
tcccatctgc cggaaggaag gcgtgctgtt ggactactct accgatggag gaattacctg    9120 gacttgctc catgagatgg attaccagaa atacattct gttagacacg actacatact    9180
tcttcctgaa gatgccctca ccaacacaac tcgacttcgc tggtggcagc cttttgtgat    9240
cagcaatgga attgtggtct ctggggtgga gcgtgctcag tgggcactgg acaacatttt    9300
gattggtgga gcagaaatca atcccagcca attggtggac acttttgatg atgaaggcac    9360 ttccatgaa gaaaactgga gttttttaccc taatgctgta aggacagcag gattttgtgg    9420
caatccatcc tttcacctct attggccaaa taaaagaag gacaagactc acaatgctct    9480
ctcctcccga gaactcatta tacagccagg atacatgatg cagtttaaaa ttgtggtggg    9540
ttgtgaagcc acttcttgtg gtgaccttca ttccgtaatg ctggaataca ctaaggatgc    9600
aagatcggat tcctggcagc tcgtacagac ccagtgcctt ccttcctctt ctaacagcat    9660
tggctgctcc cctttccagt tccatgaagc caccatctac aactctgtca acagctcaag    9720
ctggaaaaga atcaccatcc agctgcctga ccatgtctcc tctagtgcaa cacagttccg    9780
ctggatccag aagggagaag aaactgagaa gcaaagctgg gcaattgacc acgtgtacat    9840
tggagaggct tgcccaagc tctgcagcgg gcacggatac tgcacgaccg gtgccatctg    9900
catctgcgac gagagcttcc aaggtgatga ctgctctgtt ttcagtcacg accttcccag    9960
```

```
ttatattaaa gataattttg agtccgcaag agtcaccgag gcaaactggg agaccattca    10020
aggtggagtc ataggaagtg gctgtgggca gctggccccc tacgcccatg gagactcact    10080
gtactttaat ggctgtcaga tcaggcaagc agctaccaag cctctggatc tcactcgagc    10140
aagcaaaatc atgtttgttt tgcaaattgg gagcatgtcg cagacggaca gctgcaacag    10200
tgacctgagt ggcccccacg ctgtggacaa ggcagtgctg ctgcaataca gcgtcaacaa    10260
cgggatcacc tggcatgtca tcgcccagca ccagccaaag gacttcacac aagctcagag    10320
agtgtcttac aatgtccccc tggaggcacg gatgaaagga gtcttactgc gctggtggca    10380
accacgccac aatggaacag gtcatgatca atgggctttg gaccatgtgg aggtcgtcct    10440
cactcgcaaa caaaattaca tgatgaattt ttcacgacaa catgggctca gacatttcta    10500
caacagaaga cgaaggtcac ttaggcgata cccatgaaga atcaaaaagt ttattttttt    10560
tcttccaaca tgtgatgtgt tgctctccat tcttttaaat ctcgcactac atctgatatc    10620
aggaaatatc tgtgaaggac ttggtgatta cctgaaagcc cttctcaaga ccgagtgtac    10680
accactttcc cacactgtga actaatgaca agtgacttat ttgctcataa gtaaatgtct    10740
tcatgttgat gtgtccgtga aagttgtgat ctgttgtaat atcagttaca gtggcagtat    10800
tgacaataag aaacagttta acagaaaaat gaaatttaag cacaaaaaat ttaagagatt    10860
ttatgtttaa aatggcattt agcacagtat ttaacattct tggtcacaaa gctatttaag    10920
tggactgtat ttcggctatg tctcatgttt tatatgatta aattatcatt gtttgtcctt    10980
tatgtattct cttctacaat acaacacatt gaaactgtat ttacttgtta tgttgtaata    11040
ttttgctgct gaatttgggg ctacttatat tctgcagaaa attaattgaa atacctattc    11100
aagaagatag ttgtaaagat attgtatctc ctttaatata ctccttaaaa atgtatgttg    11160
gtttagcgtt gttttgtgga taagaaaaat gcttgaccct gaaatatttt ctactttaaa    11220
ttgtggatga agaccctatc tcccacaaat aagttcccat ttccttgtct aaagatcttt    11280
ttttaagtgt tctgtggctg atttactaac agtaactgcc atttttgtc tgtgataaca     11340
gagtgatttg taaaacagtg gttgtttttt cattgtgttt tcttcgtgga ttgtttttc     11400
tgcgggtcat attcatacct tctgatgaag ttgtacaaca ccagcaacat tataatggcc    11460
ctgtagctct gaatgctatt tgtgtaactg aaaggttgca ctctagggtg aaccaagcta    11520
taaaagccca tgcttaaata aaaattatgt ccaaaagcca ttgaa                    11565
```

US 10,683,366 B2

METHODS AND COMPOSITIONS FOR TREATMENT OF ATHEROSCLEROSIS

CROSS REFERENCE TO RELATED APPLICATIONS

This application is a 35 U.S.C. 371 National Stage application of International Application No. PCT/US2016/053351, filed Sep. 23, 2016, which claims the benefit of U.S. Provisional Application No. 62/233,290, filed Sep. 25, 2015 each of which is herein incorporated by reference in its entirety.

INCORPORATION OF SEQUENCE LISTING

The sequence listing that is contained in the file named "UTSW010WO_ST25.txt," which is 45,952 bytes as measured in Microsoft Windows operating system and was created on Sep. 22, 2016, is filed electronically herewith and incorporated herein by reference.

FIELD OF THE INVENTION

The present invention relates in general to the field of medicine. More specifically, the invention relates to methods and compositions for treatment of atherosclerosis.

BACKGROUND OF THE INVENTION

Atherosclerosis is a chronic inflammatory process characterized by the recruitment and transmigration of monocytes into the intima of large vessels and subendothelial accumulation of lipids and lipid-laden foam cells, resulting in plaque formation that can rupture and lead to infarction or death. Atherosclerosis is the leading cause of morbidity and mortality in western countries and thus, effective therapies for treatment and prevention of this disease are needed.

SUMMARY OF THE INVENTION

In one aspect, the invention provides a method of treatment or prevention of atherosclerosis in a subject comprising providing a therapeutic composition that decreases the activity of Reelin protein in the blood stream of the subject, wherein the treatment results in treatment or prevention of atherosclerosis in a subject or any symptoms thereof. In one embodiment, the reduction of disease symptoms comprises reduced leukocyte adhesion to the vascular wall in the subject. In another embodiment, targeting Reelin comprises reduction of Reelin protein expression or inhibition of Reelin function in the circulation of a subject. In still another embodiment, the therapeutic composition comprises a protein, a peptide, a polypeptide, an RNA molecule, a peptidomimetic, an siRNA molecule, a decoy receptor, a carbohydrate, an antibody or antibody fragment, or a small molecule, wherein said therapeutic compound targets Reelin, resulting in a reduction of Reelin concentration and/or activity in the circulation of the subject. In other embodiments, the antibody is a monoclonal antibody, or the decoy receptor is an Fc-coupled dimeric or monomeric decoy receptor. In another embodiment, the therapeutic composition performs a function comprising: (a) reducing or inhibiting the expression of a gene encoding Reelin; (b) reducing or inhibiting the expression of a Reelin protein; (c) reducing or inhibiting expression of a receptor for Reelin; (d) reducing or inhibiting the function of a Reelin protein; or (e) binding to Reelin protein in such a way that the function is reduced or eliminated. In a further embodiment, the method further comprises administering an antithrombotic drug, an antibody targeting PCSK9, or an HMG-CoA reductase inhibitor or other therapeutic agent with the potential to reduce atherosclerosis in a subject.

In another aspect, the invention provides a method for reducing leukocyte adhesion to the vascular wall in a subject, comprising introducing to the subject a therapeutic compound targeting Reelin in the circulation of the subject, wherein said treatment results in reduced leukocyte adhesion to the vascular wall. In one embodiment, targeting Reelin comprises reduction of Reelin protein expression or inhibition of Reelin function in the circulation of a subject. In another embodiment, the therapeutic compound comprises a protein, a peptide, a polypeptide, an RNA molecule, an siRNA molecule, a decoy receptor, a carbohydrate, an antibody or antibody fragment, or a small molecule, wherein said therapeutic compound targets Reelin, resulting in reduced leukocyte adhesion to the vascular wall of the subject. In another embodiment, the antibody is a monoclonal antibody. In still another embodiment, the decoy receptor is an Fc-coupled dimeric or monomeric decoy receptor. In another embodiment, the therapeutic compound performs a function comprising: (a) reducing or inhibiting the expression of a gene encoding Reelin; (b) reducing or inhibiting the expression of a Reelin protein; (c) reducing or inhibiting expression of a receptor for Reelin; (d) reducing or inhibiting the function of a Reelin protein; or (e) binding to Reelin protein in such a way that the function is reduced or eliminated. In another embodiment, the method further comprises administering an antithrombotic drug, an antibody targeting PCSK9 or an HMG-CoA reductase inhibitor to the subject. In another embodiment, the method further comprises identifying a subject suspected of having atherosclerosis or being in need of atherosclerosis treatment.

In another aspect, the invention provides a therapeutic composition for treating atherosclerosis in a subject comprising a therapeutic compound capable of being delivered in an effective amount to reduce disease symptoms and a pharmaceutically acceptable carrier. In one embodiment, the therapeutic compound comprises a protein, a peptide, a polypeptide, an RNA molecule, a peptidomimetic, an siRNA molecule, a decoy receptor, a carbohydrate, an antibody or antibody fragment, or a small molecule, wherein said therapeutic compound targets Reelin, resulting in a reduction of Reelin in the circulation of the subject.

In another aspect, the invention provides an antibody, immunological fragment, or derivative thereof which immunogically binds Reelin, for the treatment of atherosclerosis, or diseases associated therewith or resulting therefrom.

In another aspect, the invention provides an siRNA complementary to all or a portion of a Reelin mRNA sequence provided as SEQ ID NO:3-5. In one embodiment, the siRNA functions to inhibit Reelin in a subject.

BRIEF DESCRIPTION OF THE DRAWINGS

The following drawings form part of the present specification and are included to further demonstrate certain aspects of the invention. The invention may be better understood by reference to one or more of these drawings in combination with the detailed description of specific embodiments presented herein:

FIGS. 7A and 7B—Shows Reelin enhances monocyte-endothelial cell adhesion via Apoer2. (A) Monocyte adhesion to HAEC was evaluated under the following conditions: Vehicle, Mock and Reelin. Images show the endothelial cells (cobblestone shape) and adhering U937 monocytes (small, round cells). Scale bar=200 µm. (B) Summary data for A. n=6,  P<0.01. (C) and (D) HAEC transfected with control (control RNAi), double-stranded RNA targeting Vldlr (C) or Apoer2 (D) were exposed to Vehicle, Mock and Reelin, and monocyte adhesion was evaluated. In parallel, whole cell lysates were immunoblotted for Vldlr or Apoer2 and GAPDH (lower panels). n=3;  P<0.01 versus vehicle or mock control, †† P<0.01 versus control RNAi. (E) Reelin blunts VEGF-induced eNOS activation via Apoer2. HAEC were pretreated for 24 h with Mock media or Reelin, and basal and VEGF-stimulated eNOS activity was measured. n=6,  P<0.01 versus basal; ††, P<0.01 versus vehicle or Mock control. (F) HAEC transfected with control RNAi or double-stranded RNAi targeting Apoer2 were pretreated with Mock or Reelin, and basal and VEGF-stimulated eNOS activity was measured. n=6,  P<0.01 versus VEGF alone; †† P<0.01 versus control RNAi. In B-F, values are mean±SEM.

BRIEF DESCRIPTION OF THE SEQUENCES

Figure 1A:
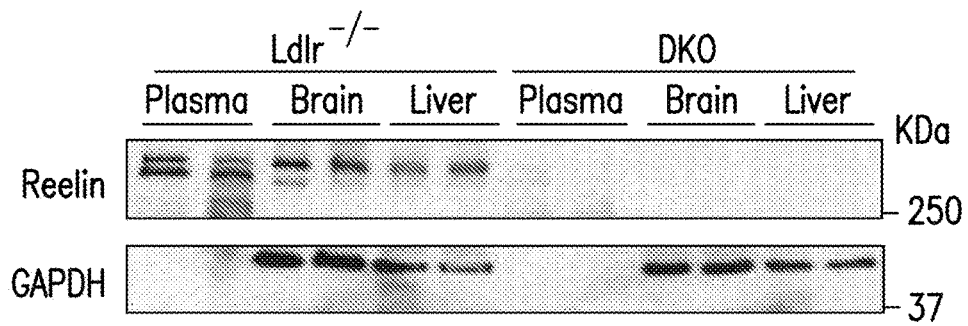
FIG. 1A-1D—Shows induction of systemic Reelin-deficiency by tamoxifen injection and analysis of plasma lipids. (A) Representative western blots analyses of Reelin in plasma, brain, and liver extract prepared from previously tamoxifen-treated two month-old Ldlr$^{-/-}$ and DKO mice. Results for two representative mice are shown for each genotype. (B) Body weight, fasting plasma triglyceride, and cholesterol levels in male Ldlr$^{-/-}$ and DKO mice after 16 weeks of high cholesterol diet. n=7-13 for each group. (C) and (D) Lipoprotein profile analysis in Ldlr$^{-/-}$ and DKO mice after fed high cholesterol diet for 16 weeks. Pooled plasma (500 µl) from 5 mice in each group was fractionated by Superose 6 chromatography and fractions were used for cholesterol (C) and triglyceride (D) determinations.

SEQ ID NO:1—Sequence of double-stranded siRNA directed to Vldlr (s14811).

SEQ ID NO:2—Sequence of double-stranded siRNA directed to Apoer2 (s15365).

SEQ ID NO:3—Sequence of the complete coding sequence of human Reelin, provided as GenBank Accession No. U79716.1.

SEQ ID NO:4—Sequence of transcript variant 1 of human Reelin, provided as GenBank Accession No. NM 005045.3.

SEQ ID NO:5—Sequence of transcript variant 2 of human Reelin, provided as GenBank Accession No. NM 173054.2.

DETAILED DESCRIPTION OF THE INVENTION

The invention provides methods and compositions for treatment or prevention of atherosclerosis in a subject comprising introduction of a therapeutic compound targeting Reelin in the circulation of the subject, wherein said treatment results in a reduction of disease symptoms in the subject. Also provided are methods and compositions for reducing leukocyte adhesion to the vascular wall in a subject, resulting in reduction of disease symptoms in the subject. In some embodiments, a therapeutic compound as described herein performs a function comprising: (a) reducing or inhibiting the expression of a gene encoding Reelin; (b) reducing or inhibiting the expression of a Reelin protein; (c) reducing or inhibiting expression of a receptor for Reelin; (d) reducing or inhibiting the function of a Reelin protein; or (e) binding to Reelin protein in such a way that the function is reduced or eliminated.

Reelin is a large, multimodular secreted, extracellular matrix glycoprotein that controls neuronal migration and positioning during brain development. It was originally found in the developing brain where it is secreted by Cajal-Retzius neurons in the marginal zone. After development, Reelin functions as a synaptic neuromodulator by binding to cognate receptors Apolipoprotein E receptor-2 (Apoer2) and very low-density lipoprotein receptor (Vldlr) in neurons. In the circulation, Reelin promotes thrombosis and hemostasis. As described in detail in the Examples below, Reelin was inducibly deleted, either ubiquitously or restricted to the circulation, in atherosclerosis-prone low-density lipoprotein receptor-deficient (Ldlr$^{-/-}$) mice, and it was found that atherosclerosis progression was markedly attenuated, with mice showing reduced lesion macrophage content and decreased expression of vascular cell adhesion molecule-1 (VCAM1) and intercellular adhesion molecule-1 (ICAM1) in the lesions. Intravital microscopy further revealed decreased leukocyte-endothelial cell adhesion in the absence of Reelin. In cultured human endothelial cells, Reelin enhanced monocyte adhesion and suppressed endothelial nitric oxide synthase (eNOS) activity in an Apoer2-dependent manner. The inventors thus discovered that circulating Reelin promotes atherosclerosis by increasing leukocyte-endothelial cell adhesion and facilitating the infiltration of inflammatory macrophages into the arterial wall via Apoer2. Targeting circulating Reelin thus presents a novel opportunity for the prevention of cardiovascular disease through prevention or reduction of leukocyte adhesion to the vascular wall.

The binding of Reelin to Apoer2 and Vldlr on the surface promotes tyrosine phosphorylation of the cytoplasmic adaptor protein disabled homolog 1 (Dab1). Phosphorylated Dab1 then activates a series of signal transduction mechanisms that control various cellular functions, including neuronal positioning during brain development, synaptic plasticity, and memory formation. Recent data from experimental and clinical studies indicate that increased Reelin expression is protective, while reduced Reelin expression is associated with several neurodegenerative disorders including Alzheimer's disease (AD).

In addition to the CNS, Reelin is found in the circulation, the liver, the pituitary pars intermedia, and in adrenal chromaffin cells. It promotes platelet spreading on fibrinogen and also plays a role in coagulation, by enhancing thrombin generation and the formation of fibrin clots. There is evidence that the two receptors for Reelin, Apoer2 (Lrp8) and Vldlr influence atherosclerosis severity. In macrophages, Apoer2 reduces stress-induced cell death and potentially retards the development of advanced atherosclerotic plaques. In contrast, macrophage Vldlr promotes atherosclerotic lesion development. Both Reelin receptors are also expressed in endothelial cells, where Apoer2 mediates the potential anti-atherogenic actions of Apolipoprotein E3.

Therapeutic Compounds or Compositions and Administration Thereof

In accordance with the invention, any therapeutic molecule that may be used to treat atherosclerosis by reducing Reelin protein expression or inhibiting its function in the circulation is within the scope of the present invention, including, but not limited to, a protein, a peptide, an RNA molecule, such as an siRNA, an antisense oligonucleotide, an antibody or antibody fragment, such as a monoclonal antibody or a polyclonal antibody, an Fc-coupled dimeric or monomeric decoy receptor, a peptidomimetic (i.e., a small protein-like chain designed to mimic a peptide) that inhibits Reelin oligomerization or receptor binding, a carbohydrate, a small molecule, and the like. In some embodiments, such therapeutic compounds target Reelin mRNA or Reelin protein to reduce the activity of Reelin in a cell or individual subject. In another embodiment, cells that express Reelin into the circulation of the subject, including, but not limited to bone marrow-derived cells and Kuppfer cells, can be targeted using a therapeutic compound described herein. In another embodiment, liposomes or viral vectors may be used to provide antibodies or other molecules of interest to a subject for targeting of Reelin. In further embodiments, a therapeutic compound described herein may be useful for targeting cells in the subject. It is envisioned that a therapeutic molecule of the invention may include, but is not limited to, an antibody or a humanized antibody targeting Reelin to reduce or eliminate its function, a siRNA or dsRNA to reduce expression of the Reelin transcript, or a decoy receptor to bind to Reelin and eliminate its function. In an embodiment, an antibody of the invention may be a humanized antibody, i.e. an antibody from a non-human species whose protein sequence has been modified to increase the similarity to antibody variants produced naturally in humans. In some embodiments, an siRNA in accordance with the invention may be complementary to all or a portion of the mRNA sequence provided as SEQ ID NO:3-5. In an embodiment, the siRNA functions to inhibit Reelin in a subject.

Any method of interfering with Reelin activity in a subject, such as inhibiting or eliminating the expression of Reelin protein or its gene in the circulation, or inhibiting or eliminating the function of Reelin protein in the circulation, known in the art may be useful in accordance with the invention. In other embodiments, a protein may be combined with a non-naturally occurring pharmaceutically acceptable carrier such as one described herein. In some embodiments, treatment methods of the present invention involve direct delivery of such a therapeutic molecule or compound. In other embodiments, treatment methods of the present invention may involve direct delivery of, for example, a vector expressing a functional copy of a therapeutic compound or molecule, such as a protein, for example a vector expressing an antibody targeting Reelin or a decoy receptor to which Reelin may bind to reduce or eliminate its function. In further embodiments, treatment may comprise any combination of delivery of a therapeutic compound as described herein, delivery of a vector expressing a therapeutic compound or protein, or a combination of these with any known treatment for atherosclerosis, including but not limited to administering an antithrombotic drug, a drug that acts in cholesterol homeostatis, such as an antibody targeting proprotein convertase subtilisin/kexin type 9 (PCSK9) or an HMG-CoA reductase inhibitor (i.e., a statin) to the subject.

Therapeutic compounds or compositions within the scope of the present invention may also contain other compounds, which may be biologically active or inactive. For example, one or more antibodies or decoy receptors described herein may be present, within a composition according to the invention. In some embodiments, antibodies or proteins useful with the present invention may be conjugated to other macromolecules. Therapeutic compounds or compositions may generally be used for prophylactic and/or therapeutic purposes. Embodiments of the invention provide therapeutic compounds or compositions for treatment of any inflammatory state involving the induction of endothelial inflammatory responses leading to or not leading to leukocyte extravasation as part of the pathogenic mechanism. In certain embodiments, therapeutic compounds or compositions provided by the invention are useful in methods of treating or preventing multiple sclerosis, where circulating monocytes aggravate or perpetuate the pathology. Other exemplary syndromes that can be treated using the compositions provided by the invention include arthritis or psoriasis, or any disorder in which excessive leukocyte/monocyte extravasation aggravates the disease process. For example, in accordance with the invention, a composition as described herein may be provided to a subject, such as a human, before onset of symptoms in order to reduce atherosclerotic plaques or to prevent the symptoms caused by atherosclerosis. In other embodiments, such a composition may be provided to a subject, such as a human, after onset of symptoms of atherosclerosis in order to provide treatment of atherosclerosis in the subject, such as by reducing or eliminating symptoms in the subject.

Therapeutic compounds or compositions may be provided to a subject in a single dose or multiple doses and as such provided in single-dose or multi-dose containers, such as sealed ampules or vials. Such containers may be sealed to preserve sterility of the composition until use. In general, compositions as described herein may be stored as suspensions, solutions, or emulsions in oily or aqueous vehicles. Alternatively, such a composition may be stored in a freeze-dried condition requiring only the addition of a sterile liquid carrier immediately prior to use.

In one embodiment, the present invention provides a treatment method for atherosclerosis or antiphospholipid syndrome, resulting from inhibition or elimination of the function of Reelin protein or the gene encoding Reelin protein, or a receptor to which Reelin binds. In certain embodiments, methods of the present invention may be used to treat or prevent atherosclerosis or antiphospholipid syndrome in a subject, or to treat any other diseases that may benefit from the use of decoy receptors for ApoER2 or Vldlr, for example.

In one embodiment, the invention thus provides a method of treating a subject with atherosclerosis or antiphospholipid syndrome, the method comprising administering or delivering to the subject a therapeutic compound, for example an antibody targeting Reelin protein or a decoy receptor for Reelin, wherein the therapeutic compound is introduced into the circulation of the subject.

In an embodiment, a nucleotide sequence encoding a therapeutic compound, for example an antibody targeting Reelin or a functional copy of a decoy receptor, may be introduced to the subject. For example, in accordance with the invention, a vector appropriate for use in a human or an animal, for example an adeno-associated viral vector, may be used to insert or transduce a nucleotide sequence encoding antibody targeting Reelin or a functional copy of a decoy receptor to the subject as described herein.

In an embodiment, the invention provides a composition comprising a therapeutic compound that targets a Reelin protein or the gene encoding Reelin. In some embodiments, an RNA molecule may be targeted through the use of an siRNA or a miRNA. In other embodiments, Reelin may be targeted through the use of a decoy receptor, such as an Fc-coupled dimeric or monomeric decoy receptor.

Accordingly, therapeutic compounds as described herein may be delivered to the subject, for instance into the circulation, through a variety of routes. In other embodiments, a vector comprising a nucleic acid sequence encoding a therapeutic compound such as an antibody targeting Reelin or a decoy receptor. In general, any administration route that places the cells into the circulation of the subject may be used. In one embodiment of the invention, the cells may be injected intravenously.

As described herein, a therapeutic composition may be combined with a pharmaceutically acceptable carrier. In some embodiments, a pharmaceutically acceptable carrier as described herein is non-naturally occurring. The selection of a suitable carrier may be determined in part by the particular composition being administered (e.g., antibody, protein, modulatory compounds, or the like), as well as by the particular method used to administer the composition. Accordingly, a wide variety of suitable formulations of therapeutic compositions are available that may of use in the present invention. Administration may be in any convenient manner, e.g., by injection, oral administration, inhalation, transdermal application, or rectal administration.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended subject, and aqueous and nonaqueous sterile suspensions that can include suspending agents, solubilizers, thickening agents, stabilizers, and preservatives. In the practice of this invention, compositions may be administered, for example, by intravenous infusion into the circulation, orally, topically, or intraperitoneally.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic, or weakly hypertonic with the blood of a subject, suspending agents, thickening agents, and/or preservatives. Alternatively, compositions of the present invention may be formulated as a lyophilizate. Compounds may also be encapsulated within liposomes using methods known in the art.

Injection solutions and suspensions may be prepared from sterile powders, granules, and tablets as described herein. An injection as described herein may involve a suspension of one or more of a purified or non-purified solution of an antibody, decoy receptor, protein, or other type of molecule as described herein. An injection solution may also contain a pharmaceutically acceptable carrier as described herein.

Formulations suitable for oral administration may consist of (a) liquid solutions, such as an effective amount of the packaged antibody, decoy receptor, protein, or other type of molecule suspended in diluents, such as water, saline or PEG 400; (b) capsules or tablets, each containing a predetermined amount of the active ingredient, as liquids, solids, granules or gelatin; (c) suspensions in an appropriate liquid; or (d) suitable emulsions. Tablet forms may include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms may comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compound of choice, alone or in combination with other suitable components, may be made into aerosol formulations to be administered via inhalation. Aerosol formulations may be placed into pressurized acceptable propellants, such as dichlorodifluoromethane, propane, nitrogen, and the like.

The dose administered to a subject in the context of the present invention should be sufficient to effect a beneficial therapeutic response in the subject over time. The dose will be determined by the efficacy of the particular molecule employed and the condition of the subject, as well as the body weight and/or surface area of the patient to be treated. The size of the dose also may be determined by the existence, nature, and extent of any adverse side-effects that accompany the administration of a particular molecule or therapeutic compound in a particular subject.

For administration, compounds and transduced cells of the present invention can be administered at a rate determined by the LD-50 of the molecule or therapeutic compound, and the side-effects thereof at various concentrations, as applied to the mass and overall health of the subject. Administration may be accomplished via single, multiple, or divided doses.

Antibody Production

Methods that may be used to produce polyclonal and monoclonal antibodies that react specifically with a Reelin protein or fragment thereof are known in the art. Such techniques may include antibody preparation by selection of antibodies from recombinant antibody libraries in phage or other vectors, as well as preparation of polyclonal and monoclonal antibodies by immunizing rabbits or mice.

A number of antigens or antigenic regions comprising a Reelin protein or portions thereof may be used to produce antibodies specifically reactive to Reelin. For example, a Reelin protein or fragment thereof, may be isolated using any methods described herein or known in the art. Recombinant proteins may be expressed in prokaryotic or eukaryotic cells and purified as described herein. Monoclonal and/or polyclonal antibodies may be produced using naturally occurring (in pure or impure form) or recombinant proteins using methods known in the art. Synthetic peptides derived from a Reelin sequence may also be used to generate antibodies and may be conjugated to a carrier protein and injected into an animal capable of producing antibodies (e.g., rabbit).

Methods of production of polyclonal antibodies are known to those of skill in the art. For example, an inbred strain of mice or rabbits may be immunized with a protein using a standard adjuvant, such as an adjuvant described herein, using a standard immunization protocol known in the art. When appropriately high titers of antibody to the protein are obtained, antisera may be prepared and enrichment performed to obtain antibodies reactive to the protein.

Monoclonal antibodies may also be obtained by various methods known in the art. For example, spleen cells from an animal immunized with a desired antigen may be immortalized, commonly by fusion with a myeloma cell or through transformation with Epstein Barr Virus (EBV), oncogenes, or retroviruses, or other methods well known in the art. The immortalized cells may then be screened for production of antibodies of the desired specificity and affinity for the antigen. Yield of the monoclonal antibodies produced by such cells may be enhanced by various techniques known in the art, for example by injection into the peritoneal cavity of a vertebrate host.

Monoclonal antibodies and polyclonal sera may be collected and titered against the desired antigen or protein (e.g., Reelin protein) in an immunoassay, for example, a solid phase immunoassay with the protein immobilized on a solid support. Antibodies specific only for a Reelin protein may also be made by subtracting out other cross-reacting proteins. In this manner, antibodies that bind only to the protein of choice may be obtained.

Hybridomas may be employed to produce antibodies in accordance with the invention, in which a hybrid cell line may be used as the basis for the production of antibodies in large quantities for diagnostic or therapeutic use. A hybridoma may be produced by injecting an antigen such Reelin protein into a mammal such as a mouse, collecting monoclonal antibody-producing cells produced thereby, and fusing the antibodies with a tumor cell to produce myelomas.

Once the specific antibodies against the desired antigen, such as a Reelin protein, are available, the desired antigen may be detected using a variety of immunoassay methods.

The antibody may also be a humanized antibody for therapeutic use with a non-natural, pharmaceutically acceptable carrier.

Protein either associated with or distinct from a Reelin protein may be detected and/or quantified using any of a number of well recognized immunological binding assays. Immunological assays may use an antibody that specifically binds to a protein or antigen of choice. The antibody may be produced by any of a number of methods well known to those of skill in the art. Immunoassays may also use a labeling agent to specifically bind to the complex formed by the antibody and antigen for detection purposes. The labeling agent may itself be one of the moieties comprising the antibody/antigen complex. Thus, the labeling agent may be a labeled Reelin protein antibody. Alternatively, the labeling agent may be a third moiety, such as a secondary antibody, that specifically binds to the antibody/antigen complex. A secondary antibody may be specific to antibodies of the species from which the first antibody is derived. A labeling agent can be modified with a detectable moiety, such as biotin, to which another molecule can specifically bind, such as streptavidin. A variety of detectable moieties are well known to those skilled in the art.

Immunoassays for detecting a protein such as Reelin in samples are well known in the art. Such assays may be either competitive or noncompetitive, and may be either quantitative or non-quantitative. Noncompetitive immunoassays are assays in which antigen may be directly detected and, in some instances, the amount of antigen directly measured. In competitive assays, Reelin protein present in a sample is detected indirectly by a detectable signal associated with a known, added (exogenous) antigen displaced from an antibody by the antigen present in a sample. In this manner, such assays can also be adapted to provide for an indirect measurement of the amount of Reelin protein present in the sample. Competitive binding immunoassays may also be used to determine cross-reactivity, in which any cross-reacting antibodies may be removed from pooled antisera. Additional assay types, including but not limited to western blot or liposome immunoassays may also be used in accordance with the present invention.

One of skill in the art will appreciate that it is often desirable to minimize nonspecific binding in immunoassays. Particularly, where the assay involves an antigen or antibody immobilized on a solid substrate it is desirable to minimize the amount of nonspecific binding to the substrate. Means of reducing such non-specific binding are well known to those of skill in the art.

An assay as described herein may include a label or detectable group that does not significantly interfere with the specific binding of the antibody used in the assay. A detectable group may be any material having a detectable physical or chemical property. Such detectable labels are known in the art and generally, any label useful in such methods may be applied to the present invention. Thus, a "label" as used herein may be any composition detectable by spectroscopic, photochemical, biochemical, immunochemical, electrical, optical or chemical means. Useful labels in the present invention may include magnetic beads (e.g., DYNABEADS™), fluorescent dyes (e.g., fluorescein isothiocyanate, Texas red, rhodamine, and the like), radiolabels (e.g., $^3H$, $^{125}I$, $^{35}S$, $^{14}C$, or $^{32}P$), enzymes (e.g., horse radish peroxidase, alkaline phosphatase, and/or any others known in the art and used in ELISA), and colorimetric labels such as colloidal gold or colored glass or plastic beads (e.g., polystyrene, polypropylene, latex, etc.).

A label in accordance with the invention may be coupled directly or indirectly to the desired component of the assay according to methods well known in the art. As described above, a wide variety of labels may be used, with the choice of label depending on sensitivity, ease of conjugation with the compound, stability requirements, or available instrumentation, among others.

Non-radioactive labels may be attached by indirect means. Generally, a ligand molecule (e.g., biotin) is covalently bound to the molecule. The ligand may then bind to another molecule (e.g., streptavidin), which may be either inherently detectable or covalently bound to a signal system, such as a detectable enzyme, a fluorescent compound, or a chemiluminescent compound. The ligands and their corresponding targets may be used in any suitable combination with antibodies that recognize a Reelin protein, or secondary antibodies that recognize a Reelin protein. The molecules may also be conjugated directly to signal generating compounds, e.g., by conjugation to an enzyme or fluorophore. Enzymes of interest to be used as labels may be hydrolases, for example phosphatases, esterases and glycosidases, or oxidotases, such as peroxidases. Fluorescent compounds may include fluorescein and its derivatives, rhodamine and its derivatives, dansyl, umbelliferone, and the like. Chemiluminescent compounds may include luciferin, 2,3-dihydrophthalazinediones, e.g., luminol, or others known in the art.

Means of detecting labels are well known to those of skill in the art and will depend on the type of label used. For example, autoradiography may be used to detect a radioactive label, or fluorochromes may be used to detect a fluorescent label. Fluorescence may be detected visually, for example by electronic detectors such as charge coupled devices (CCDs) or photomultipliers, and the like. Similarly, enzymatic labels may be detected by providing the appropriate substrates for the enzyme and detecting the resulting reaction product. Colorimetric or chemiluminescent labels may be detected by observing a color associated with a particular label. In some embodiments, an assay formats may not require the use of a labeled component but rather may be detected by simple visual inspection.

Post-Transcriptional Gene Suppression

As used herein the words "gene suppression," is intended to refer to any of the well-known methods for reducing the levels of protein produced as a result of gene transcription to mRNA and subsequent translation of the mRNA. Gene suppression is also intended to mean the reduction of protein expression from a gene or a coding sequence including posttranscriptional gene suppression and transcriptional suppression. Post-transcriptional gene suppression is mediated by the homology between of all or a part of a mRNA transcribed from a gene or coding sequence targeted for suppression and the corresponding double stranded RNA used for suppression, and refers to the substantial and measurable reduction of the amount of available mRNA available in the cell for binding by ribosomes. The transcribed RNA can be in the sense orientation to effect what is called co-suppression, in the anti-sense orientation to effect what is called anti-sense suppression, or in both orientations producing a double stranded RNA (dsRNA) to effect what is called RNA interference (RNAi). Transcriptional suppression is mediated by the presence in the cell of a dsRNA, a gene suppression agent, exhibiting substantial sequence identity to a promoter DNA sequence or the complement thereof to effect what is referred to as promoter trans suppression. Gene suppression may be effective against a native gene associated with a trait, e.g., to suppress expression of a Reelin protein.

Post-transcriptional gene suppression may employ both sense-oriented and anti-sense-oriented, transcribed RNA which is stabilized, e.g., as a hairpin and stem and loop structure. A preferred DNA construct for effecting post transcriptional gene suppression one in which a first segment encodes an RNA exhibiting an anti-sense orientation exhibiting substantial identity to a segment of a gene targeted for suppression, which is linked to a second segment encoding an RNA exhibiting substantial complementarity to the first segment. Such a construct would be expected to form a stem and loop structure by hybridization of the first segment with the second segment and a loop structure from the nucleotide sequences linking the two segments.

The present invention provides dsRNA or siRNA molecules for reduction or elimination of Reelin expression. siRNA technology is known in the art and used to study inhibition of, for example, apolipoprotein receptors such as ApoCIII (Gaudet et al., *N Engl J Med* 373(5):438-47, 2015; Graham et al., *Circulation Res* 112:1479-1490, 2013) ApoA (Tsimikas et al., *Lancet* 2015), or chemicals useful in accordance with the invention, such as PCSK9 (Miao et al., *Arterioscler Thromb Vasc Biol* 35(7):1589-96, 2015). The dsRNA or siRNA nucleotide sequences comprise double strands of polymerized ribonucleotide and may include modifications to either the phosphate-sugar backbone or the nucleoside. Modifications in RNA structure may be tailored to allow specific genetic inhibition. In one embodiment, the dsRNA molecules may be modified through an enzymatic process so the siRNA molecules may be generated. The siRNA can efficiently mediate the down-regulation effect for some target genes. This enzymatic process may be accomplished by utilizing an RNAse III enzyme or a DICER enzyme, present in the cells of an individual in the eukaryotic RNAi pathway. Both the DICER enzyme and RNAse III, naturally occurring in an individual or made through recombinant DNA techniques, cleave larger dsRNA strands into smaller oligonucleotides. The DICER enzymes specifically cut the dsRNA molecules into siRNA pieces each of which is about 19-25 nucleotides in length while the RNAse III enzymes normally cleave the dsRNA molecules into 12-15 base-pair siRNA. The siRNA molecules produced by the either of the enzymes have 2 to 3 nucleotide 3' overhangs, and 5' phosphate and 3' hydroxyl termini. The siRNA molecules generated by RNAse III enzyme are the same as those produced by Dicer enzymes in the eukaryotic RNAi pathway and are hence then targeted and degraded by an inherent cellular RNA-degrading mechanism after they are subsequently unwound, separated into single-stranded RNA and hybridize with the RNA sequences transcribed by the target gene. This process results in the effective degradation or removal of the RNA sequence encoded by the nucleotide sequence of the target gene. The outcome is the silencing of a particularly targeted nucleotide sequence within the individual.

Inhibition of a target gene using the stabilized dsRNA technology of the present invention is sequence-specific in that nucleotide sequences corresponding to the duplex region of the RNA are targeted for genetic inhibition. RNA containing a nucleotide sequences identical to a portion of the target gene is preferred for inhibition. RNA sequences with insertions, deletions, and single point mutations relative to the target sequence have also been found to be effective for inhibition. In performance of the present invention, it is preferred that the inhibitory dsRNA and the portion of the target gene share at least from about 80% sequence identity, about 85% identity, about 90% sequence identity, about 91% identity, about 92% identity, about 93% identity, about 94% identity, or from about 95% sequence identity, about 96% identity, about 97% identity, about 98% identity, about 99% sequence identity, or about 100% sequence identity. Alternatively, the duplex region of the RNA may be defined functionally as a nucleotide sequence that is capable of hybridizing with a portion of the target gene transcript. A less than full length sequence exhibiting a greater homology compensates for a longer less homologous sequence. The length of the identical nucleotide sequences may be at least about 20, 21, 22, 23, 24, 25, 30, 35, 40, 45, 50, 60, 70, 80, 90, 100, 200, 300, 400, 500, or at least about 1000 bases. Normally, a sequence of greater than 20-100 nucleotides may be used, or a sequence of greater than about 200-300 nucleotides, or a sequence of greater than about 500-1000 nucleotides, depending on the size of the target gene. A dsRNA or siRNA as described herein may be able to tolerate sequence variations that might be expected due to genetic mutation, polymorphism, or evolutionary divergence. The introduced nucleic acid molecule may not need to be absolute homology, may not need to be full length, relative to either the primary transcription product or fully processed mRNA of the target gene. Therefore, those skilled in the art will understand that 100% sequence identity between the RNA and the target gene is not required to practice the present invention.

The dsRNA or siRNA molecules may be synthesized either in vivo or in vitro. The dsRNA may be formed by a single self-complementary RNA strand or from two complementary RNA strands. Endogenous RNA polymerase of the cell may mediate transcription in vivo, or cloned RNA polymerase can be used for transcription in vivo or in vitro. Inhibition may be targeted by specific transcription in an organ, tissue, or cell type; stimulation of an environmental condition (e.g., infection, stress, temperature, chemical inducers); and/or engineering transcription at a developmental stage or age. The RNA strands may or may not be polyadenylated; the RNA strands may or may not be capable of being translated into a polypeptide by a cell's translational apparatus.

The RNA, dsRNA, siRNA, or miRNA of the present invention may be produced chemically or enzymatically by one skilled in the art through manual or automated reactions or in vivo in another organism. RNA may also be produced by partial or total organic synthesis; any modified ribonucleotide can be introduced by in vitro enzymatic or organic synthesis. The use and production of an expression construct are known in the art. If synthesized chemically or by in vitro enzymatic synthesis, the RNA may be purified prior to introduction into the cell. For example, RNA can be purified from a mixture by extraction with a solvent or resin, precipitation, electrophoresis, chromatography, or a combination thereof. Alternatively, the RNA may be used with no or a minimum of purification to avoid losses due to sample processing. The RNA may be dried for storage or dissolved in an aqueous solution. The solution may contain buffers or salts to promote annealing, and/or stabilization of the duplex strands.

As used herein, the term "nucleic acid" refers to a single or double-stranded polymer of deoxyribonucleotide or ribonucleotide bases read from the 5' to the 3' end. The "nucleic acid" may also optionally contain non-naturally occurring or altered nucleotide bases that permit correct read through by a polymerase and do not reduce expression of a polypeptide encoded by that nucleic acid. The term "nucleotide sequence" or "nucleic acid sequence" refers to both the sense and antisense strands of a nucleic acid as either individual single strands or in the duplex. The term "ribonucleic acid" (RNA) is inclusive of RNAi (inhibitory RNA), dsRNA (double stranded RNA), siRNA (small interfering RNA), mRNA (messenger RNA), miRNA (micro-RNA), tRNA (transfer RNA, whether charged or discharged with a corresponding acylated amino acid), and cRNA (complementary RNA) and the term "deoxyribonucleic acid" (DNA) is inclusive of cDNA and genomic DNA and DNA-RNA hybrids. The words "nucleic acid segment", "nucleotide sequence segment", or more generally "segment" will be understood by those in the art as a functional term that includes both genomic sequences, ribosomal RNA sequences, transfer RNA sequences, messenger RNA sequences, operon sequences and smaller engineered nucleotide sequences that express or may be adapted to express, proteins, polypeptides or peptides.

Kits

In still further embodiments, the present invention provides kits for use with the methods described herein for treatment of atherosclerosis in a subject, for instance comprising a composition or therapeutic compound as described herein for targeting Reelin in a subject such as a canine, a feline, a mouse, or a human. Such a kit may include one or more antibodies targeting a Reelin protein or fragment thereof. A kit may further contain a decoy receptor such as an Fc-coupled dimeric or monomeric decoy receptor for administration to a subject. The kit may include one or more sterile containers, for example a vial, a tube, a flask, or a syringe.

In further embodiments, the kit may include one or more tubes or wells of a culture or microtiter plate or other cell sterile cell culture plates or flasks into which components or reagents may be placed. The kit may allow for a single sample, or more than one sample. In some embodiments, the kit may include a plurality of plates or tubes, which allow for numerous samples concurrently or consecutively.

The treatment reagents of the kit may take any one of a variety of forms. Such reagents may include, but are not limited to, media, diluents, or cell culture reagents known in the art and useful with the methods of the invention, for example, fetal bovine serum, antibiotics, or the like. Detection assays that are associated with and/or linked to a given therapeutic agent or protein may be included in a kit according to the invention. Detectable labels that are associated with and/or attached to a secondary binding ligand are also contemplated. Exemplary secondary ligands are those secondary antibodies that have binding affinity for the first antibody. A number of exemplary assays are known in the art and/or all such assays may be employed in connection with the present invention. Assays for some therapeutic compounds envisioned may be performed at certified analytical laboratories. When this is the case, the kits may include instructions and materials for submitting samples to the appropriate certified labs for analysis.

The kits may optionally include a suitably aliquoted composition of a therapeutic agent of the invention to serve as a control. The components of the kits may be packaged either in aqueous media and/or in lyophilized form, and may be suitable for storage at any temperature. In another embodiment, kits of the present invention may comprise instructions or written directions for use of the kit.

Definitions

As used herein, an "antibody" refers to a polypeptide comprising a framework region from an immunoglobulin gene or fragments thereof that specifically binds and recognizes an antigen, such as a Reelin protein or fragment thereof. The recognized immunoglobulin genes may include the kappa, lambda, alpha, gamma, delta, epsilon, and mu constant region genes, as well as the myriad immunoglobulin variable region genes. Light chains may be classified as either kappa or lambda. Heavy chains may be classified as gamma, mu, alpha, delta, or epsilon, which in turn define the immunoglobulin classes, IgG, IgM, IgA, IgD, and IgE, respectively.

An exemplary immunoglobulin (antibody) structural unit may comprise a tetramer, with each tetramer composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain and variable heavy chain refer to these light and heavy chains.

Antibodies exist, e.g., as intact immunoglobulins or as a number of well-characterized fragments produced by digestion with various peptidases. While various antibody fragments are defined in terms of the digestion of an intact antibody, one of skill will appreciate that such fragments may be synthesized de novo either chemically or by using recombinant DNA methodology. Thus, the term "antibody," as used herein, also includes antibody fragments either produced by the modification of whole antibodies, or those synthesized de novo using recombinant DNA methodologies or those identified using other methods known in the art.

For preparation of antibodies, e.g., recombinant, monoclonal, or polyclonal antibodies, many technique known in the art may be used. The genes encoding the heavy and light chains of an antibody of interest can be cloned from a cell and used to produce a recombinant monoclonal antibody. Gene libraries encoding heavy and light chains of monoclonal antibodies may also be used. Random combinations of the heavy and light chain gene products generate a large pool of antibodies with different antigenic specificity. Techniques for the production of single chain antibodies or recombinant antibodies are found in the art and may be adapted to produce antibodies to polypeptides according to the invention. Phage display technology may also be used to identify antibodies and heteromeric fragments that specifically bind to selected antigens. Antibodies may also be made bispecific, i.e., able to recognize two different antigens, or heteroconjugates, e.g., two covalently joined antibodies, or immunotoxins.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins. Thus, under particular immunoassay conditions, a specified antibody may bind to a particular protein at least two times the background and more typically more than 10 to 100 times background. Specific binding to an antibody under such conditions requires an antibody that is selected by virtue of its specificity for a particular protein. For example, polyclonal antibodies raised to a Reelin protein, polymorphic variants, alleles, orthologs, and variants thereof, or splice variants, or portions thereof, may be selected to obtain only those polyclonal antibodies that are specifically immunoreactive with Reelin and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein.

The phrase "functional effects" in the context of assays for testing compounds that modulate activity of Reelin includes the determination of a parameter that is indirectly or directly under the influence of Reelin, e.g., a phenotypic or chemical effect. "Functional effects" may include in vitro, in vivo, and ex vivo activities and may be measured by any means known to those skilled in the art, such as changes in spectroscopic characteristics, shape, chromatographic, or solubility properties for a protein, measuring inducible markers or transcriptional activation of a protein; measuring binding activity or binding assays, e.g. binding to antibodies; measuring changes in ligand or substrate binding activity, measuring cell surface marker expression, measurement of changes in protein levels, measurement of RNA stability, identification of downstream or reporter gene expression via, for example, chemiluminescence, fluorescence, colorimetric reactions, antibody binding, and/or inducible markers.

As used herein, "autologous" refers to a protein, cell, cell type, or the like, that is derived from the same individual who is to be treated. For example, in accordance with the invention, an autologous cell is a cell or a sample of cells that are isolated from an individual subject (e.g., a canine or human), transduced with a construct comprising a polynucleotide sequence encoding a protein of interest, expanded in culture to create a population of cells all of which comprise the construct, and injected back into the same subject for treatment.

The terms "inhibitors," activators," and "modulators" of Reelin nucleic acid or polypeptide sequences are used to refer to activating, inhibitory, or modulating molecules identified using in vitro and in vivo assays of the Reelin nucleic acid and polypeptide sequences. Inhibitors are compounds that may bind to, partially or totally block activity, decrease, prevent, delay activation, inactivate, desensitize, or down regulate the activity or expression of Reelin. Activators refer to compounds that increase, open, activate, facilitate, enhance activation, sensitize, agonize, or upregulate Reelin activity. Inhibitors, activators, or modulators also include genetically modified versions of Reelin, e.g., versions with altered activity, as well as naturally occurring and synthetic ligands, substrates, antagonists, agonists, antibodies, peptides, cyclic peptides, nucleic acids, antisense molecules, ribozymes, small chemical molecules and the like. Assays for inhibitors and activators include, e.g., expressing Reelin in vitro, in cells, or cell membranes, applying putative modulator compounds, and then determining the functional effects on activity, as described herein.

Test samples or assays comprising Reelin that are treated with a potential activator, inhibitor, or modulator may be compared to a control sample lacking the inhibitor, activator, or modulator in order to determine the extent of inhibition. Control samples to which a test sample or assay is compared may be assigned a relative protein activity value of 100%. Inhibition of Reelin is achieved when the activity value of the test sample relative to the control sample is less than about 80%, including about 75%, about 70%, about 65%, about 60%, 5%, a 55%, about 50%, about 45%, about 40%, about 35%, about 30%, about 25%, about 20%, about 15%, about 10%, about 5%, and about 0%.

The terms "identical" or "percent identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., the NCBI web site found at ncbi.nlm.nih.gov/BLAST/or the like). Such sequences are then referred to as "substantially identical." This definition also refers to, or applies to, the compliment of a particular sequence. The definition may also include sequences that have deletions, additions, and/or substitutions. Likewise, this definition also is intended to apply to complementarity between sequences.

For sequence comparison, one sequence typically serves as a reference sequence, to which other sequences are compared. When using a sequence comparison algorithm, reference and comparison sequences may be entered into a computer, and sequence algorithm program parameters are selected as desired. Percent sequence identities are then generated for the comparison sequences relative to the reference sequence, based on the parameters selected. An example of an algorithm that may be suitable for determining percent sequence identity and sequence similarity are the BLAST and BLAST 2.0 algorithms, which are described in Altschul et al., (*Nuc Acids Res* 25:3389-3402, 1977) and Altschul et al., (*J Mol Biol* 215:403-410, 1990), respectively. BLAST and BLAST 2.0 are well known in the art and may be used to determine percent sequence identity for any nucleic acids or proteins, such as those described herein.

The present invention includes DNA molecules or siRNA molecules and proteins having at least about 80% (percent) sequence identity, about 81% sequence identity, about 82% sequence identity, about 83% sequence identity, about 84% sequence identity, about 85% sequence identity, about 86% sequence identity, about 87% sequence identity, about 88% sequence identity, about 89% sequence identity, about 90% sequence identity, about 91% sequence identity, about 92% sequence identity, about 93% sequence identity, about 94% sequence identity, about 95% sequence identity, about 96% sequence identity, about 97% sequence identity, about 98% sequence identity, about 99% sequence identity, or about 100% sequence identity to a Reelin coding sequence provided herein, for instance the Reelin sequences set forth as SEQ ID NOs: 3-5. As used herein, the term "percent sequence identity" or "% sequence identity" refers to the percentage of identical nucleotides or amino acids in a linear polynucleotide or polypeptide sequence of a reference ("query") sequence (or its complementary strand) as compared to a test ("subject") sequence (or its complementary strand) when the two sequences are optimally aligned (with appropriate nucleotide or amino acid insertions, deletions, or gaps totaling less than 20 percent of the reference sequence over the window of comparison). Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and by computerized implementations of these algorithms such as GAP, BESTFIT, FASTA, and TFASTA available as part of the Sequence Analysis software package of the GCG® Wisconsin Package® (Accelrys Inc., San Diego, Calif.), MEGAlign (DNAStar, Inc., 1228 S. Park St., Madison, Wis. 53715), and MUSCLE (version 3.6) (RC Edgar, Nucleic Acids Research (2004) 32(5):1792-1797) with default parameters. An "identity fraction" for aligned segments of a test sequence and a reference sequence is the number of identical components which are shared by the two aligned sequences divided by the total number of components in the reference sequence segment, that is, the entire reference sequence or a smaller defined part of the reference sequence. Percent sequence identity is represented as the identity fraction multiplied by 100. The comparison of one or more sequences may be to a full-length sequence or a portion thereof, or to a longer sequence.

Proteins in accordance with the invention may be produced by changing (that is, modifying) a wild-type protein to produce a new protein with a novel combination of useful protein characteristics, such as altered Vmax, Km, substrate specificity, substrate selectivity, and protein stability. Modifications may be made at specific amino acid positions in a protein and may be a substitution of the amino acid found at that position in nature (that is, in the wild-type protein) with a different amino acid. Proteins provided by the invention thus provide a new protein with one or more altered protein characteristics relative to the wild-type protein found in nature. In one embodiment of the invention, a protein may have altered protein characteristics such as improved or decreased activity against one or more herbicides or improved protein stability as compared to a similar wild-type protein, or any combination of such characteristics. In one embodiment, the invention provides a Reelin antibody, and the DNA molecule or coding sequence encoding it, having at least about 80% sequence identity, about 81% sequence identity, about 82% sequence identity, about 83% sequence identity, about 84% sequence identity, about 85% sequence identity, about 86% sequence identity, about 87% sequence identity, about 88% sequence identity, about 89% sequence identity, about 90% sequence identity, about 91% sequence identity, about 92% sequence identity, about 93% sequence identity, about 94% sequence identity, about 95% sequence identity, about 96% sequence identity, about 97% sequence identity, about 98% sequence identity, about 99% sequence identity, or about 100% sequence identity to a protein sequence such as set forth as SEQ ID NO:3-5. Amino acid mutations may be made as a single amino acid substitution in the protein or in combination with one or more other mutation(s), such as one or more other amino acid substitution(s), deletions, or additions. Mutations may be made as described herein or by any other method known to those of skill in the art.

As used herein, the term "nucleic acid" refers to a single or double-stranded polymer of deoxyribonucleotide bases or ribonucleotide bases read from the 5' to the 3' end. A "nucleic acid" may also optionally contain non-naturally occurring or altered nucleotide bases that permit correct read through by a polymerase and do not reduce expression of a polypeptide encoded by that nucleic acid. The term "nucleotide sequence" or "nucleic acid sequence" refers to both the sense and antisense strands of a nucleic acid as either individual single strands or in the duplex. The term "ribonucleic acid" (RNA) is inclusive of RNAi (inhibitory RNA), dsRNA (double stranded RNA), siRNA (small interfering RNA), mRNA (messenger RNA), miRNA (micro-RNA), tRNA (transfer RNA, whether charged or discharged with a corresponding acylated amino acid), and cRNA (complementary RNA). The terms "nucleic acid segment," "nucleotide sequence segment," or more generally, "segment," will be understood by those in the art as a functional term that includes genomic sequences, ribosomal RNA sequences, transfer RNA sequences, messenger RNA sequences, operon sequences, and smaller engineered nucleotide sequences that express or may be adapted to express, proteins, polypeptides or peptides. The nomenclature used herein is that required by Title 37 of the United States Code of Federal Regulations § 1.822 and set forth in the tables in WIPO Standard ST.25 (1998), Appendix 2, Tables 1 and 3.

The term "gene" refers to components that comprise viral DNA or RNA, cDNA, viral intron and exon DNA, artificial viral DNA polynucleotide, or other DNA that encodes a peptide, polypeptide, protein, or RNA transcript molecule, and the genetic elements that may flank the coding sequence that are involved in the regulation of expression, such as, promoter regions, 5' leader regions, 3' untranslated region that may exist as native genes or transgenes in the genome. The gene or a fragment thereof can be subjected to polynucleotide sequencing methods that determines the order of the nucleotides that comprise the gene.

Polynucleotides as described herein may be complementary to all or a portion of a gene sequence, including a promoter, intron, coding sequence, exon, 5' untranslated region, and 3' untranslated region.

A particular nucleic acid sequence may also encompass "splice variants." Similarly, a particular protein encoded by a nucleic acid implicitly encompasses any protein encoded by a splice variant of that nucleic acid. "Splice variants" are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

Macromolecular structures such as polypeptide structures may be described in terms of various levels of organization. "Primary structure" refers to the amino acid sequence of a particular peptide. "Secondary structure" refers to locally ordered, three dimensional structures within a polypeptide. These structures are commonly known as domains, for example enzymatic domains, extracellular domains, transmembrane domains, pore domains, or cytoplasmic tail domains. Domains are portions of a polypeptide that form a compact unit of the polypeptide. Exemplary domains include domains with enzymatic activity. A domains may be made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The phrase "treating atherosclerosis" or "treatment of atherosclerosis" refers to ameliorating the effects of, or delaying, halting, or reversing the progress of, or delaying or preventing the onset of, atherosclerosis as defined herein.

As used herein, a "therapeutic compound" or "therapeutic composition" refers to a molecule, such as an antibody or antibody fragment, such as a monoclonal antibody or a polyclonal antibody, RNA molecule, protein, peptide, polypeptide, an Fc-coupled dimeric or monomeric decoy receptor, a peptidomimetic that inhibits Reelin oligomerization or receptor binding a carbohydrate, a small molecule, or the like, that has the activity of reducing or eliminating Reelin protein expression or inhibit its function. Such a compound or composition is meant to encompass a composition suitable for administration to a subject, such as a mammal, particularly a human subject. In general a "therapeutic composition" is sterile, and preferably free of contaminants that are capable of eliciting an undesirable response within the subject (e.g., the compound(s) in the immunogenic composition is pharmaceutical grade). Therapeutic compositions may be designed for administration to subjects in need thereof via a number of different routes of administration including oral, intravenous, buccal, rectal, parenteral, intraperitoneal, intradermal, intratracheal, intramuscular, subcutaneous, inhalational, and the like.

As used herein, "subject" or "patient" refers to animals, including humans, who are treated with the therapeutic compounds or compositions or in accordance with the methods described herein. For diagnostic or research applications, a wide variety of mammals may be suitable subjects, including rodents (e.g., mice, rats, hamsters), rabbits, primates, and swine, such as inbred pigs and the like.

As used herein, a "biological sample" or "sample" may include blood and blood parts including, but not limited to serum, plasma, platelets, or red blood cells; sputum, mucosa, tissue, cultured cells, including primary cultures, and transformed cells; biological fluids, stool, and urine. A biological sample may also include sections of tissues such as biopsy and autopsy samples, and frozen sections taken for histologic purposes. A biological sample may be obtained from a eukaryotic organism, such as a human. Any tissue appropriate for use in accordance with the invention may be used, for instance, skin, brain, spinal cord, adrenals, pectoral muscle, lung, heart, liver, duodenum, small intestine, large intestine, kidney, spleen, pancreas, adrenal gland, bone marrow, lumbosacral spinal cord, or blood.

As used herein, a "pharmaceutically acceptable carrier," "pharmaceutically acceptable adjuvant," or "adjuvant" refers to refers to reagents, cells, compounds, materials, compositions, and/or dosage forms that are not only compatible with the antibodies or other agents to be administered therapeutically, but also are, within the scope of sound medical judgment, suitable for use in contact with the tissues of human beings and animals without excessive toxicity, irritation, allergic response, or other complication commensurate with a reasonable benefit/risk ratio. Also included may be an agent that modifies the effect of other agents and is useful in preparing a therapeutic compound or composition that is generally safe, non-toxic, and neither biologically nor otherwise undesirable. Such an agent may be added to a therapeutic composition to modify the immune response of a subject by boosting the response such as to give a higher amount of antibodies and longer-lasting protection. Such an agent may include an excipient, diluent, carrier, or adjuvant that is acceptable for pharmaceutical use. Such an agent may be non-naturally occurring, or may be naturally occurring, but not naturally found in combination with other agents in the immunogenic composition.

The term "isolated compound" means a compound which has been substantially separated from, or enriched relative to, other compounds with which it occurs in nature. Isolated compounds are usually at least about 80%, at least 90% pure, at least 98% pure, or at least about 99% pure, by weight.

The term "unit dosage form," as used herein, refers to physically discrete units suitable as unitary dosages for animal subjects, each unit containing a predetermined quantity of a compound (e.g., a Reelin antibody as described herein) calculated in an amount sufficient to produce the desired effect in association with a pharmaceutically acceptable diluent, carrier, or vehicle. The specifications for unit dosage forms depend on the particular compound employed, the route and frequency of administration, the effect to be achieved, and the pharmacodynamics associated with each compound in the host.

As used herein, "cell culture," "in culture," or "cultured" refers generally to cells taken from a living organism and grown under controlled conditions. A "primary cell culture" is a culture of cells, tissues, or organs taken directly from an organism before the first subculture. Cells are expanded in culture when they are placed in a growth medium under conditions that facilitate growth and/or division, resulting in a larger population of the cells. When cells are expanded in culture, the rate of cell proliferation is sometimes measured by the amount of time needed for the cells to double in number, referred to as "doubling time."

As used herein, "introducing," "delivering," and "administering" refer to the therapeutic introduction of a therapeutic compound or composition as described herein to a subject. Administration may take place by any route that provides the therapeutic compound to the circulation of the subject in accordance with the invention.

The phrase "effective amount" refers to a concentration or amount of a therapeutic compound or composition as described herein, reagent, or other agent, that is effective for producing an intended result, including treatment of atherosclerosis as described herein. With respect to the administration of a therapeutic compound as disclosed herein, an effective amount may be any effective range or concentration. The exact dose will depend on the purpose of the treatment, and one of skill in the art will be able to determine such a dose using techniques known in the art.

As used herein, "expression" refers to the combination of intracellular processes, including transcription and translation undergone by a coding DNA molecule such as a structural gene to produce a polypeptide or functional nucleic acid (e.g., an RNAi, antisense molecule, ribozyme, aptamer, etc.).

As used herein, "genetic Transformation" refers to a process of introducing a DNA sequence or construct (e.g., a vector or expression cassette) into a cell or protoplast in which that exogenous DNA is incorporated into a chromosome or is capable of autonomous replication.

The term "about" is used herein to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When not used in conjunction closed wording in the claims or specifically noted otherwise, the words "a" and "an" denote "one or more."

The terms "comprise," "have," and "include" are openended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any cell that "comprises," "has" or "includes" one or more traits is not limited to possessing only those one or more traits and covers other unlisted traits.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Animal Models

Mice carrying the loxP-targeted Reln gene (encoding Reelin protein) were generated by gene targeting murine SV129J ES cells as described previously (Lane-Donovan, et al. *Science Signaling* 8, 2015) and mated with Ldlr−/− (Ishibashi, et al. *The Journal of Clinical Investigation* 92:883-893, 1993) mice to yield double homozygotes (Relnfl/fl;Ldlr−/−). Reelinfl/fl;Ldlr−/− mice were then crossbred with CAG-CreETR2 mice (Jackson strain #004682) to obtain CAG-Cre+ Reelinfl/fl;Ldlr−/− mice and their Crenegative littermates. To induce Cre-mediated DNA recombination, 6 week-old Relnfl/fl;Ldlr−/− mice with or without the CAG-Cre transgene were intraperitoneally injected with 0.135 mg/g body weight tamoxifen dissolved in sunflower oil for 5 consecutive days to yield global Reelin and Ldlr double knockout (DKO) mice, and Ldlr−/− (control) mice. To elucidate the role of circulating Reelin in atherogenesis, 6 week-old Relnfl/fl;Ldlr−/− mice were intravenously injected with either adenovirus vector encoding Cre recombinase (Ad-Cre) to generate mice lacking circulating Reelin (Ad-Cre Relnfl/fl;Ldlr−/−), or with adenovirus vector encoding β-Galactosidase (Ad-Gal) to generate control mice (Ad-Gal Relnfl/fl;Ldlr−/−). The Ad-Cre and Ad-Gal were produced as described previously (Rohlmann, et al. *Nature Biotechnology* 14:1562, 1996). Two weeks following injection with either tamoxifen or adenovirus, Reelin levels in the plasma, brain and liver were determined by western blotting. To evaluate atherosclerosis severity, eight-week-old male mice of each genotype, i.e. lacking or expressing Reelin, were placed on an atherogenic high cholesterol diet containing 21% (w/w) milk fat, 1.25% (w/w) cholesterol and 0.5% (w/w) cholic acid (TD 02028, Harlan Laboratories, Indianapolis, Ind.). In select experiments, white blood cell (WBC) counts and differentials were performed by collecting fresh blood obtained via retro-orbital bleeding in EDTA-containing tubes. A ProCyte Dx Hematology Analyzer (IDEXX Laboratories) was used to quantify the five major WBC subpopulations: neutrophils, lymphocytes, monocytes, eosinophils and basophils.

Example 2

Cell Culture and Transfection

Human aortic endothelial cells (HAEC, Cambrex Corp.) were cultured in EBM2 medium (Lonza) containing 10% FBS and used within 3-6 passages. The monocyte cell line U937 (human histiocytic lymphoma, ATCC) was grown in RPMI 1640 medium (Sigma-Aldrich) containing 10% FBS. In siRNA experiments, HAEC were transfected using siPORT amine transfection reagent (Life Technologies). Double-stranded siRNA directed to Vldlr (s14811) with the functional sequence GCAGUGUAAUGGUAUCCGAtt (SEQ ID NO: 1) or directed to Apoer2 (s15365) with the functional sequence CAUCCCUAAUCUUCACCAAtt (SEQ ID NO:2) were purchased from Life Technologies, and control siRNA was from GE HEALTHCARE DHARMACON INC (D0018100250). The siRNA-mediated silencing of Apoer2 or Vldlr expression was evaluated by immunoblot analysis.

Example 3

Immunoblot Analysis

Protein samples from plasma, tissues or HAEC whole cell lysates were prepared in RIPA buffer and separated by SDS-PAGE. After transfer onto nitrocellulose membranes (Bio-Rad), blots were probed separately with monoclonal mouse anti-Reelin (G10; Bergeyck, et al. *Journal of Neuroscience Methods* 82:17, 1998), rabbit anti-mouse Apoer2 and monoclonal mouse anti-Vldlr antibodies as indicated in the Figures. The Vldlr antibody was purchased from Millipore Corporation (Cat # MABS25) and the Apoer2 antibody was generated as described previously (Beffert, et al. *Journal of Neuroscience* 26:2041, 2006). The secondary antibody used was HRP-linked anti-mouse IgG or anti-rabbit IgG (GE Healthcare), and membranes were visualized with SuperSignal West Pico Chemiluminescence reagents and X-ray film. Band intensity was quantified using scanning densitometry of non-saturating autoradiograms with ImageJ software (NIH) within linear exposure range.

Example 4

Plasma Lipids and Lipoprotein Profiles

At termination, blood was collected from mice via tail bleeding after an overnight fasting period, and plasma was separated by centrifugation. Plasma lipids (total cholesterol and triglyceride) were determined using kits from Thermo Scientific Company. HDL-cholesterol (HDL-C) was quantified after precipitation of apolipoprotein B-containing lipoproteins with an equal volume of a 20% polyethylene glycol solution. Lipoprotein profiles were determined by fractionation of pooled 500 µl plasma from 5 mice in each group using a Superose 6 column (Amersham Pharmacia).

Example 5

Atherosclerotic Lesion Analysis

Mice fed a high cholesterol diet for 16 weeks were euthanized by anesthetic overdose. Hearts were perfused with PBS and 4% paraformaldehyde, and hearts and entire aorta were collected. For en face analysis, entire aortas from the heart extending 5-10 mm beyond the bifurcation of the iliac arteries were removed and dissected free of adjoining tissues, opened, and stained with Oil red O. Lesion extent was evaluated by morphometry of scanned images using ImageJ software. For the analysis of lesions in the aortic sinus, serial cryosections of 10 µm thickness were taken from the region of the proximal aorta through the aortic sinuses and stained with Oil red O or hematoxylin. Quantitative immunostaining was performed using primary antibodies against Mac-3 (1:200; BD Pharmingen™), α-smooth muscle actin (1:200; Abcam), CD106 (1:40; BD Pharmingen™) or CD54 (1:40; R&D systems), and fluorescently-labeled secondary antibodies goat anti-rat Alexa Fluor 488 (ThermoFisher Scientific, A11006), donkey anti-goat Alexa Fluor 594 (ThermoFisher Scientific, A11058), or goat anti-rabbit Alexa Fluor 594 (ThermoFisher Scientific, A11012). Nuclei were counterstained with DAPI (ThermoFisher Scientific, P36935). Images were obtained with a Zeiss Axiophot microscope and the percentage of lesion area that was positively stained was determined using ImageJ software (NIH).

Example 6

Intravital Microscopy for Quantification of Leukocyte-Endothelial Cell Adhesion

Leukocyte-endothelial adhesion was evaluated as described previously (Umetani, et al. Cell Metab., 2014). Briefly, 3-week-old male mice were intraperitoneally injected with vehicle or tamoxifen daily for 5 days. After tamoxifen-mediated knockdown of circulating Reelin was confirmed by immunoblotting, the mice were prepared for intravital microscopy. Endogenous leukocytes were fluorescence labeled by injection with Rhodamine-6G (100 µl of 0.05% solution given via optic vascular plexus), and the mesentery was exposed for the observation and recording of images of leukocyte adhesion and rolling using a Regita digital camera (QImaging). The velocity and quantity of leukocyte rolling was measured by Image-Pro v.6.2 (Media-Cybernetics). In preliminary studies the effects of tamoxifen on adhesion were evaluated in Relnfl/fl; Ldlr-/- mice treated daily for 5 days with tamoxifen or vehicle. WBC velocity was similar in tamoxifen-treated and vehicle-treated mice.

Example 7

Monocyte Adhesion Assay

The adhesion of U937 monocytes to monolayers of HAEC was evaluated as previously described (Ramesh, et al. The Journal of Clinical Investigation 121:120, 2011). Recombinant Reelin and mock conditioned media were collected and purified by column chromatography and size exclusion filtration from the supernatant of stably-transfected 293 cells and nontransfected 293 cells, respectively. Confluent HAEC were treated with vehicle, mock media (20 µl per 1 ml) or Reelin (20 µl per 1 ml) for 16 h. Subsequently HAEC were washed with PBS and rinsed with RPMI 1640 medium, U937 monocytes (1×106 cells/well) were added and incubated with HAEC under rotating conditions (benchtop incubator at 70 rpm) at 37° C. for 20 min, nonadhered monocytes were removed by gentle washing with PBS, cells were fixed with 1% paraformaldehyde for 10 min at room temperature, and the number of adherent cells was determined in triplicate per ×40 magnification field by Image J software. In select studies HAEC were transfected with control, Apoer2 or Vldlr siRNA prior to the treatment with mock media or Reelin.

Example 8

Endothelial Nitric Oxide Synthase Activation Assay

Endothelial nitric oxide synthase (eNOS) activation was determined in intact endothelial cells by measuring the conversion of [14C]L-arginine to [14C]l-citrulline. Briefly, HAEC were pretreated with vehicle, mock media or Reelin for 30 min, and eNOS activity was then assessed over 15 min in the continued presence of vehicle, mock media or Reelin, in the absence (basal) or presence of VEGF (100 ng/ml). Findings were replicated in 3 or more independent experiments.

Example 9

Statistical Analyses

All data are expressed as mean±SEM. Two-tailed Student's t test or one-way ANOVA was used to assess differences between two groups or among more than two groups, respectively, with Newman-Keuls post-hoc testing following one-way ANOVA. P values <0.05 (*) were considered significant, or highly significant (p<0.01, **).

Example 10

Generation and Characterization of Conditional Reln-/-;Ldlr-/- Mice

To explore the potential role of Reelin in the pathogenesis of atherosclerosis, Ldlr$^{-/-}$ mice were crossed with floxed Reln mice expressing a tamoxifen-inducible Cre recombinase under the control of the ubiquitously active CAG promoter. Cre-negative littermates were used as controls.

Figure 2A:
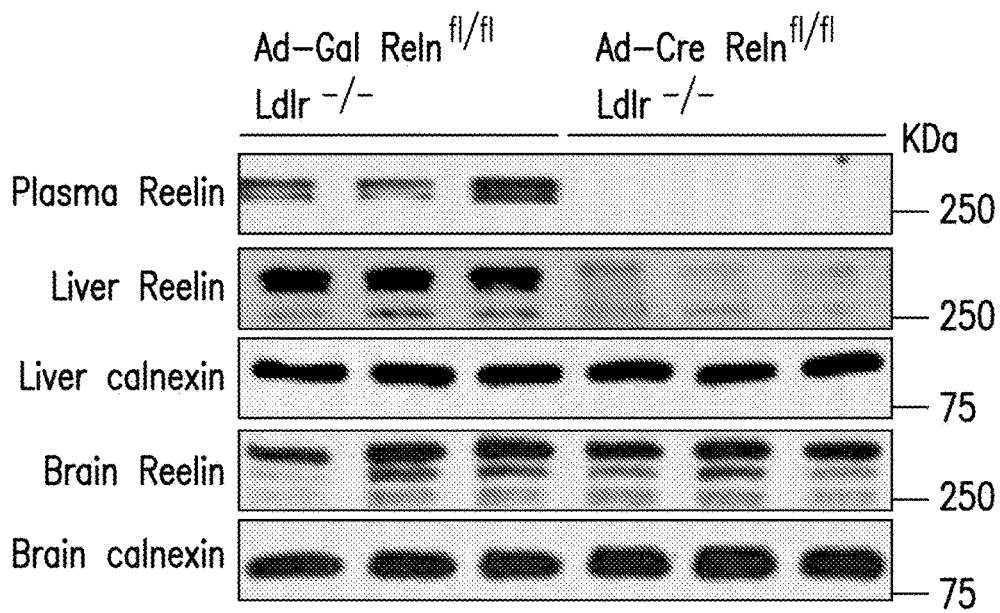
FIGS. 2A and 2B—Shows generation of circulating Reelin deficiency using adenoviral delivery of Cre recombinase. (A) Western blot analysis for Reelin abundance in plasma and tissues obtained 2 weeks after jugular vein infusion of adenoviruses encoding either Cre recombinase or a β-Gal control. Samples for 3 mice per group are shown. (B) After fed high cholesterol diet for 16 weeks, body weight, plasma triglyceride, total cholesterol, and HDL-cholesterol levels were determined in fasted animals. n=8 animals per group, values are mean±SEM, * P<0.05 versus Ad-Gal-Reln$^{fl/fl}$ Ldlr$^{-/-}$.

After intraperitoneal injection of tamoxifen for two weeks, immunoblot analysis confirmed the deletion of Reelin protein in the plasma, brains and livers of the double knockout (DKO) mice (FIG. 1A). To segregate the potential effects of circulating Reelin on atherosclerosis from those of systemic Reelin, mice with selective deletion of Reelin only in plasma were generated by injecting $Reln^{fl/fl}$; $Ldlr^{-/-}$ mice through the tail vein with adenovirus expressing Cre recombinase (Ad-Cre). Adenovirus expressing P3-galactosidase (Ad-Gal) served as control. Immunoblot analysis demonstrated efficient and specific ablation of Reelin from the liver and from plasma, but not from the brain in the Ad-Cre-injected $Reln^{fl/fl}$;$Ldlr^{-/-}$ mice (FIG. 2A).

Figure 1B:
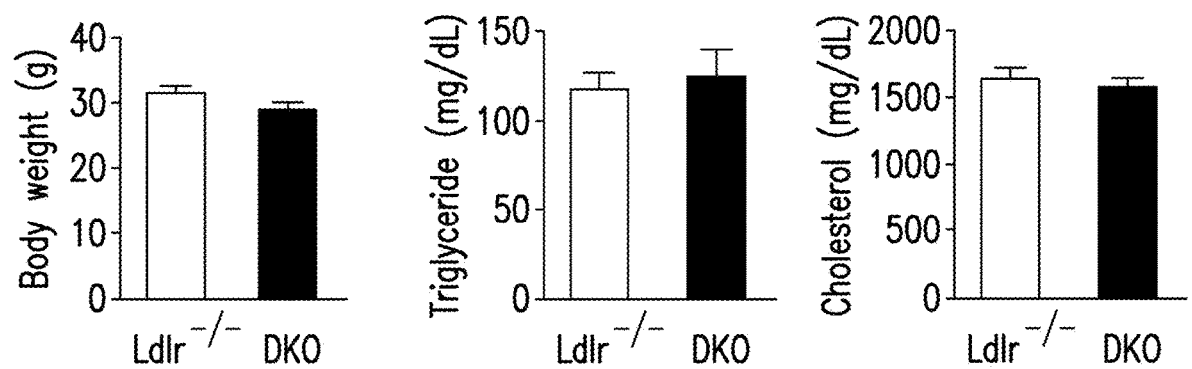
Figure 1C:
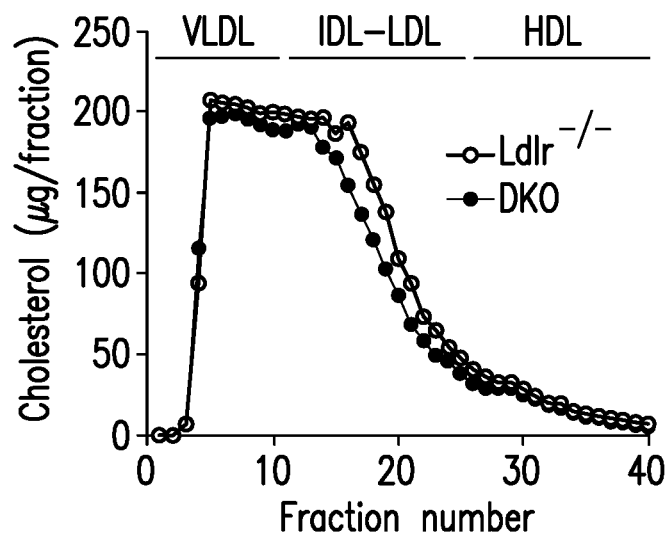
Figure 1D:
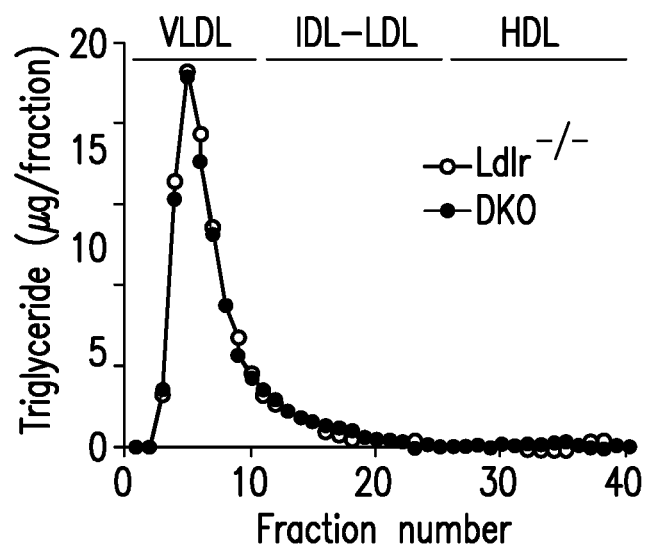
Figure 2B:
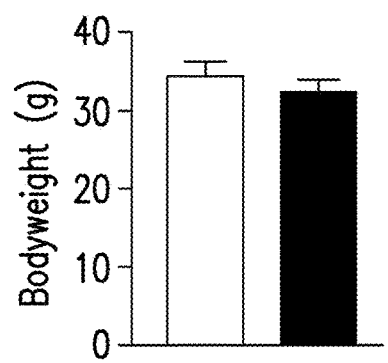
Figure 2B:
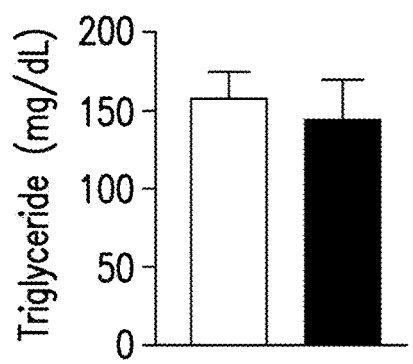
Figure 2B:
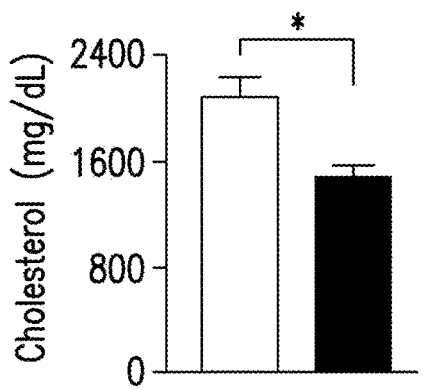
Figure 2B:
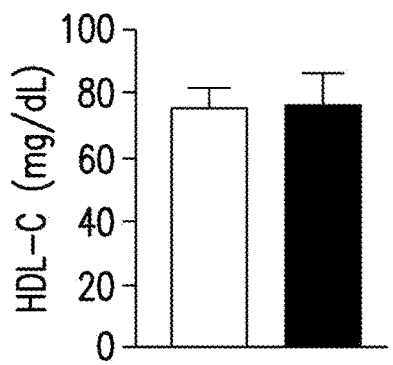

Plasma lipid parameters were determined in all mice after feeding with a high cholesterol diet for 16 weeks. As shown in FIG. 1B, no differences in body weight, plasma cholesterol or triglyceride levels were observed between DKO mice and $Ldlr^{-/-}$ mice, and the atherogenic diet caused similarly severe hypercholesterolemia with comparable lipid profiles for cholesterol and triglyceride in the two groups of mice (FIG. 1C, D). In the adenovirus treated groups, total plasma cholesterol was modestly increased in Ad-Gal $Reln^{fl/fl}$;$Ldlr^{-/-}$ mice compared to Ad-Cre $Reln^{fl/fl}$;$Ldlr^{-/-}$ mice, while plasma triglyceride and HDL-cholesterol (HDL-C) levels were similar in the two groups (FIG. 2B).

Example 11

Reelin Deficiency Reduces Atherosclerosis in Ldlr-/- Mice

Figure 3A:
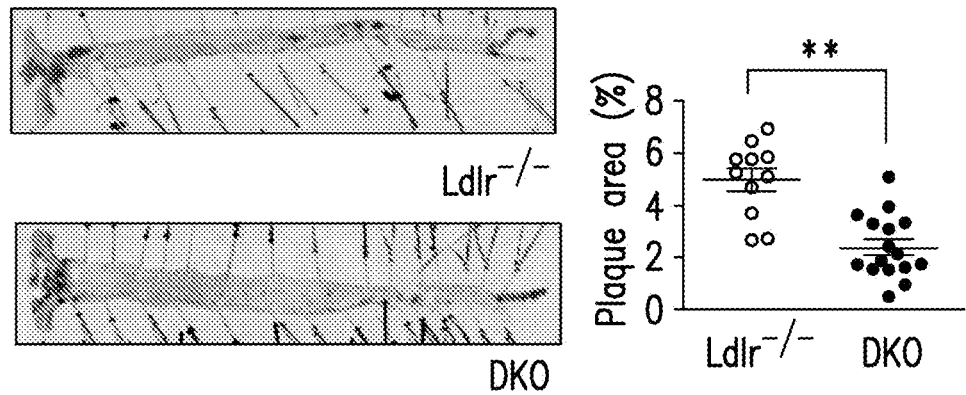
FIGS. 3A and 3B—Shows global Reelin deficiency attenuates atherosclerotic lesion development in Ldlr$^{-/-}$ mice. (A) Representative en face photomicrographs and lesion analyses for whole aorta in male Ldlr$^{-/-}$ and DKO mice. (B) Representative photomicrographs of aortic root sections stained with Oil Red O and quantification of atheroma area in Ldlr$^{-/-}$ and DKO mice (Scale bar=200 µm). n=10-16 animals per group. In A and B, data represent mean±SEM; ** P<0.01 vs Ldlr$^{-/-}$.
Figure 3B:
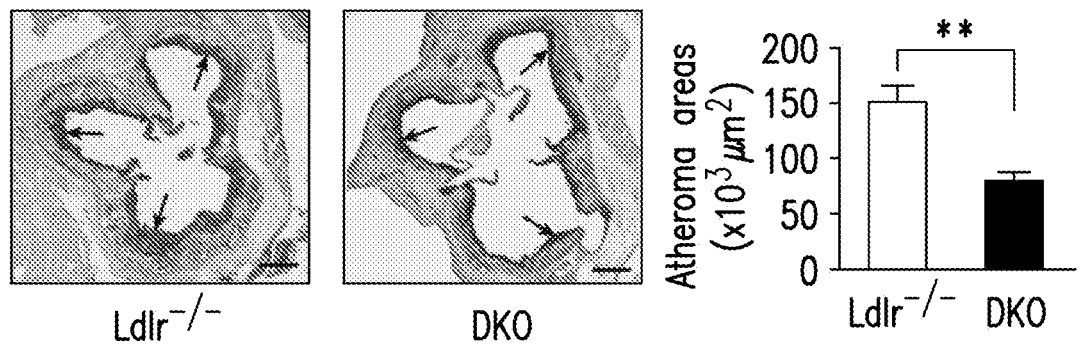
Figure 4A:
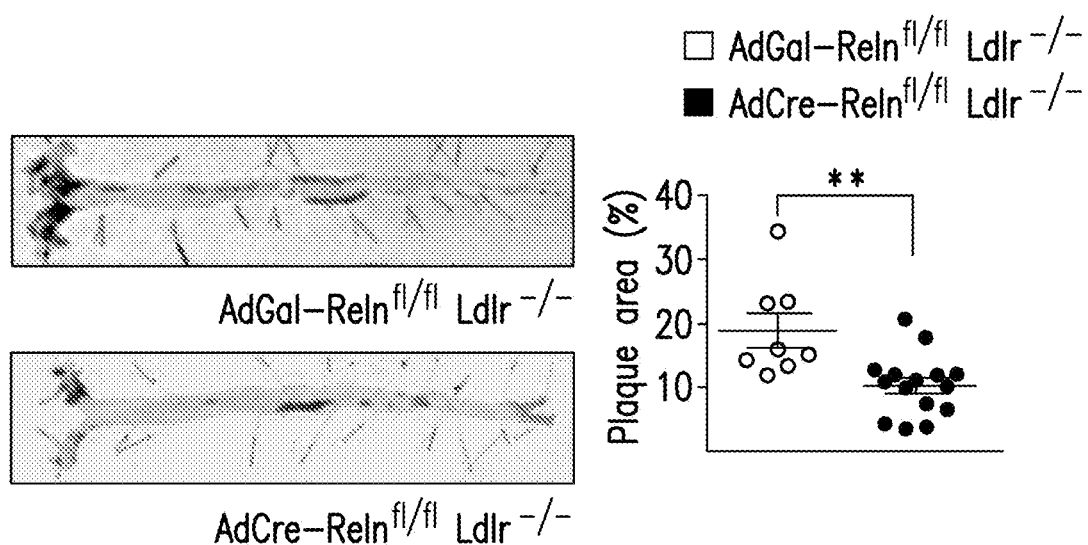
FIGS. 4A and 4B—Shows knockdown of circulating Reelin decreases atherosclerotic lesion size in Ad-Cre-Reln$^{fl/fl}$ Ldlr$^{-/-}$ mice. (A) Representative en face photomicrographs and lesion analyses for whole aorta in Ad-Cre-Relnfl/fl Ldlr-/- and Ad-Gal-Reln$^{fl/fl}$ Ldlr$^{-/-}$ mice. (B) Representative photomicrographs of aortic root sections stained with Oil Red O and quantification of atheroma area in Ad-Cre-Reln$^{fl/fl}$ Ldlr$^{-/-}$ and Ad-Gal-Reln$^{fl/fl}$ Ldlr$^{-/-}$ mice. Scale bar=200 m, arrows indicate atherosclerotic lesions. n=6 animals per group. In A and B, data represent mean±SEM; ** P<0.01 vs Ad-Gal-Reln$^{fl/fl}$ Ldlr$^{-/-}$.
Figure 4B:
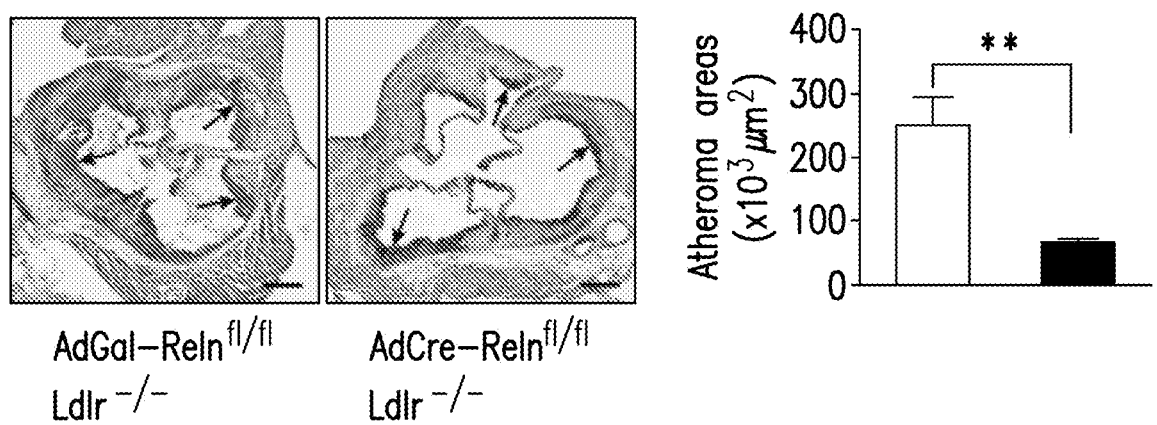

Following high cholesterol feeding for 16 weeks beginning at eight weeks of age, aortas were excised and stained with Oil Red-O to visualize atherosclerotic plaques. En face analyses revealed a 52% decrease in atherosclerotic lesion area in aortas from DKO mice with global Reelin deletion compared to the aortas of control $Ldlr^{-/-}$ mice (FIG. 3A). As shown in FIG. 3B, quantitative analysis of lesion areas in cross-sections of the aortic sinus showed a similar 47% reduction in lesion size in DKO mice compared to controls. Similarly, Ad-Cre $Reln^{fl/fl}$;$Ldlr^{-/-}$ mice displayed a 46% decrease of atherosclerotic lesion area in the aorta and a 73% reduction of aortic root lesions compared with Ad-Gal Relnfl/fl;Ldlr-/- mice (FIGS. 4A and 4B). Thus, both global and plasma-selective Reelin deficiency greatly diminished atherosclerotic lesion formation.

Example 12

Figure 5A:
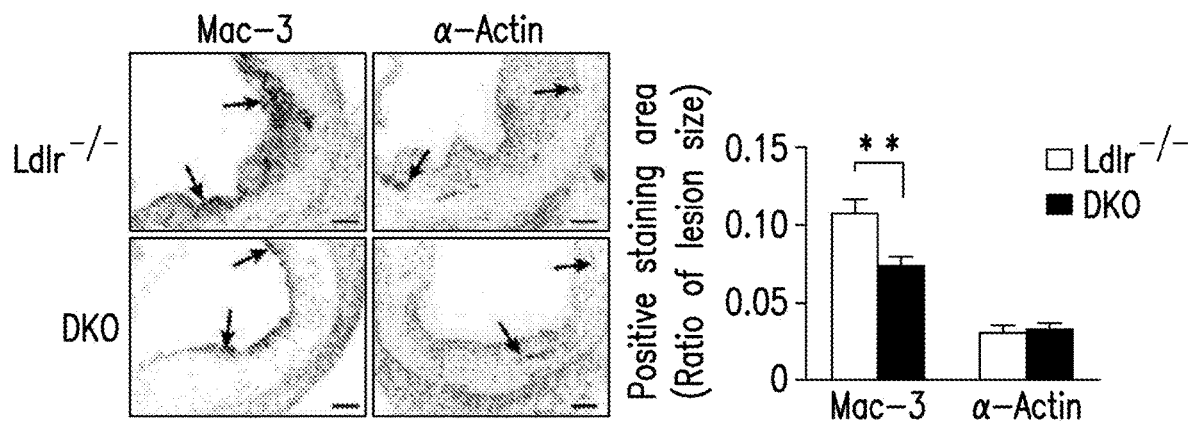
FIGS. 5A and 5B—Shows Global Reelin deficiency decreases monocyte recruitment to atherosclerotic lesions in Ldlr$^{-/-}$ mice. (A) Representative aortic root cross-sections stained with anti-Mac-3 and anti-α-actin antibodies to detect macrophage (green) and smooth muscle cell accumulation (red). (B) Representative aortic sinus sections stained for VCAM1 and ICAM1. In (A) and (B), sections were counterstained with DAPI (blue) to stain nuclei, and size bars represent 50 µm. Positive staining is indicated by the white arrows. In (A) and (B), bar graphs show summary data for area of positive staining normalized to lesion area, with at least 3 fields of view used to calculate an average for each section. N=7/group, data represent mean±SEM; ** P<0.01 compared to Ldlr$^{-/-}$.

Reelin Deficiency Reduces Adhesion Molecule Expression and Macrophage Infiltration The presence of macrophages and smooth muscle cells in atherosclerotic plaques from DKO and control $Ldlr^{-/-}$ mice was investigated by immunostaining with anti-Mac-3 and anti-α-actin antibodies, respectively. As shown in FIG. 5A, morphometric quantification of the lesions revealed a 32% reduction of Mac-3 positive macrophages in DKO versus $Ldlr^{-/-}$ control mice. No difference in α-actin-positive (smooth muscle) area was observed between the two groups.

Figure 5B:
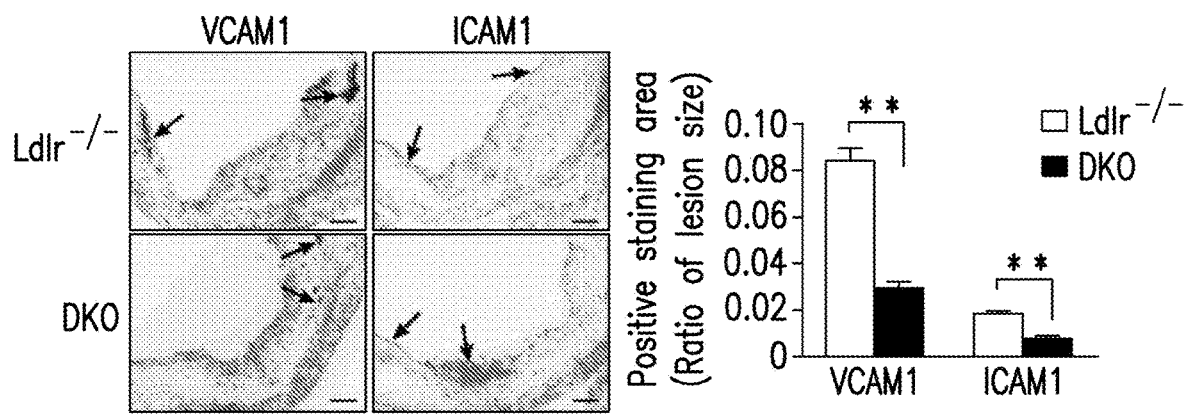

The migration of monocytes into the subendothelium of arteries in atherosclerosis results from the activation of endothelial cells, which leads to the increased expression of leukocyte adhesion molecules. To determine the basis for the impact of Reelin on lesion macrophage accumulation, VCAM-1 and ICAM-1 expression in plaques was investigated by immunostaining with anti-CD106 and anti-CD54 antibodies, respectively. VCAM-1 was reduced by 65% and ICAM-1 by 56% in plaques from DKO mice compared to $Ldlr^{-/-}$ mice (FIG. 5B). At the same time, Mac-3, CD106 and CD54 immunoreactivity was similarly reduced in the lesions of Ad-Cre $Reln^{fl/fl}$;$Ldlr^{-/-}$ compared to Ad-Gal $Reln^{fl/fl}$;$Ldlr^{-/-}$ mice (data not shown). These results suggest that Reelin promotes macrophage foam cell accumulation in atherosclerotic lesions, and that this is driven by increased adhesion molecule expression.

Example 13

Reelin Increases Leukocyte-Endothelial Cell Adhesion

Figure 6A:
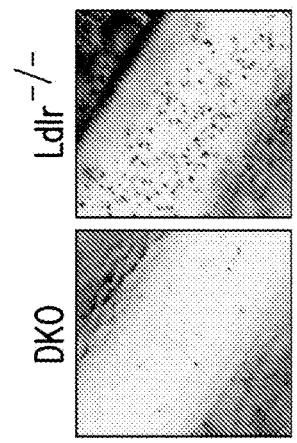
FIGS. 6A, 6B, and 6C—Shows Global Reelin deficiency reduces leukocyte-endothelial cell adhesion, and it has no effect on circulating WBC number. (A) After peritoneal injection of tamoxifen daily for 5 d, intravital microscopy was performed in male Ldlr$^{-/-}$ and DKO mice to evaluate leukocyte-endothelial cell adhesion in the mesenteric microcirculation. Representative still images are shown. (B) Summary data for leukocyte velocity and the number of adherent leukocytes. Values are mean±SEM, n=10 for each group, * P<0.05, ** P<0.01 compared to Ldlr$^{-/-}$ control group. (C) Total WBC count and numbers of leukocyte subtypes were determined in Ldlr$^{-/-}$ and DKO mice (MO, monocyte; LY, lymphocyte; NE, neutrophils; EO, eosinophil; BA, basophil). n=6 for each group, data represent mean±SEM.
Figure 6B:
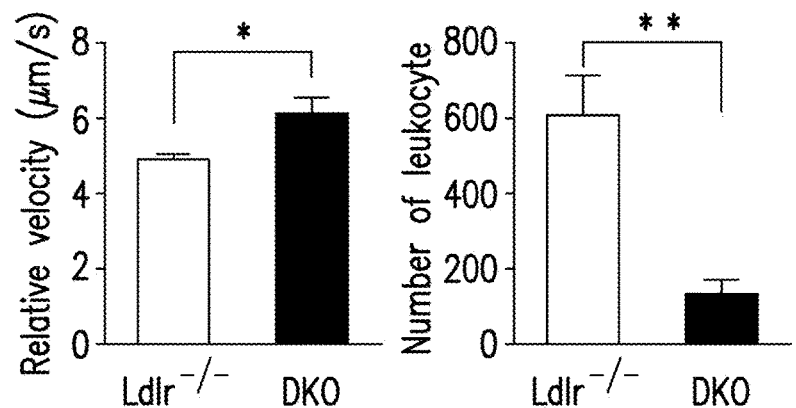
Figure 6C:
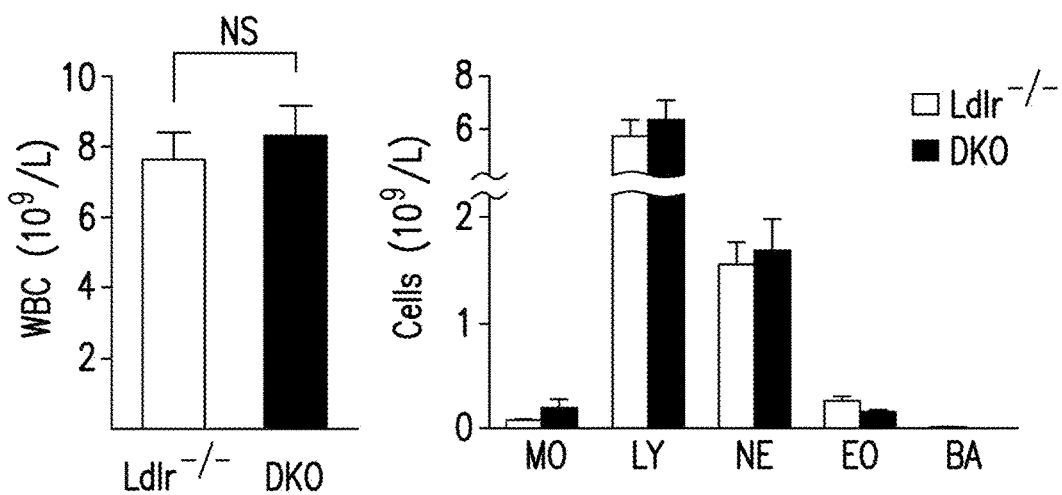

To better understand the mechanisms by which Reelin promotes macrophage accumulation in atherosclerosis, intravital microscopy was performed to quantify leukocyte-endothelial adhesion in vivo in the setting of low versus high Reelin abundance. Male DKO and $Ldlr^{-/-}$ mice were intraperitoneally injected for 5 days with tamoxifen, and the tamoxifen-induced reduction of circulating Reelin was confirmed by western blotting. Endogenous leukocytes were fluorescently labeled by injection of Rhodamine-6G, and intravital video microscopy was performed to visualize leukocyte adhesion to the endothelium in the mesenteric microvasculature. As shown in representative still images in FIG. 6A and in the quantitation provided in FIG. 6B, leukocyte velocity was increased by 25% and the number of adherent leukocytes was reduced by 78% in DKO mice compared with $Ldlr^{-/-}$ mice. Total circulating WBC and leukocyte subsets were also quantified in DKO and $Ldlr^{-/-}$ mice, and no differences were observed (FIG. 6C). Therefore, the intravital microscopy findings are not the result of an effect of Reelin on leukocyte abundance, but they instead they indicate that Reelin increases leukocyte-endothelial cell adhesion in vivo.

To determine if direct actions of Reelin on endothelial cells underlie the apparent increase in adhesion, and if these processes are operative in human endothelium, monocyte adhesion to cultured primary human aortic endothelial cells (HAEC) was investigated. Compared with vehicle and Mock treatment of HAEC, Reelin caused a >2-fold increase in adhesion (FIGS. 7A and 7B). To determine which Reelin receptor mediates the increase in endothelial cell-monocyte adhesion, siRNA knockdown of Vldlr or Apoer2 was performed. Whereas loss of Vldlr did not alter the effect of Reelin (FIG. 7C), Apoer2 knockdown effectively prevented the Reelin mediated increase of endothelial cell-monocyte adhesion (FIG. 7D). These results indicate that Reelin enhances adhesion via Apoer2 and not Vldlr in endothelium.

Example 14

Reelin Antagonizes Endothelial NOS Through Apoer2

NO generated by endothelial eNOS is a key modulator of leukocyte-endothelial cell adhesion. Having previously shown that Apoer2 mediates antiphospholipid antibody-induced suppression of eNOS, which increases endothelial cell-leukocyte adhesion, it was next investigated whether Reelin alters eNOS activity in HAEC and whether Apoer2 participates. eNOS activation by VEGF was quantified by measuring 14C-arginine conversion to 14C-citrulline in intact HAEC. Whereas VEGF increased eNOS activity in non-treated and Mock-treated cells, Reelin potently attenuated eNOS activation (FIG. 7E). As shown in FIG. 7F, siRNA knockdown of Apoer2 fully prevented Reelin-mediated inhibition of eNOS activation. Thus, Reelin reduces eNOS activity via Apoer2.

Example 15

Figure 8:
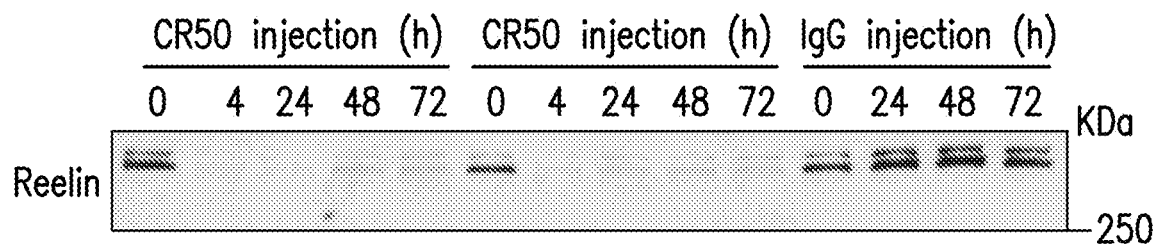
FIG. 8—Shows sustained reduction of plasma Reelin abundance in mice after intraperitoneal injection of the anti-Reelin antibody CR50. Plasma samples were collected at the indicated time points from CR50 or mouse IgG injected mice. Reelin was measured by Western blot. Representative Western blots are shown.

Treatment with Anti-Reelin Antibody Reduces Monocyte and Leukocyte Adhesion in the Vascular Endothelium The effect of a reduction in plasma Reelin abundance on monocyte and leukocyte adhesion was investigated using the anti-Reelin antibody CR50 (RIKEN). Intraperitoneal injection of CR50 resulted in sustained reduction of plasma Reelin in mice (FIG. 8).

Figure 9:
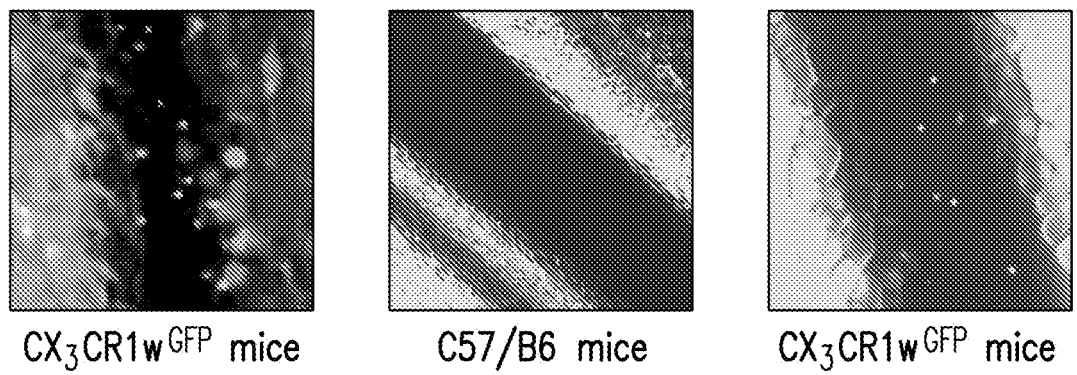
FIG. 9—Shows selective labeling of circulating monocytes in C57/B6 and CX$_3$CR1w$^{GFP}$ mice. Representative still images are shown.

An in vivo leukocyte adhesion assay was developed in which monocytes were selectively labeled in $CX_3CR1w^{GFP}$ mice (FIG. 9).

Figure 10:
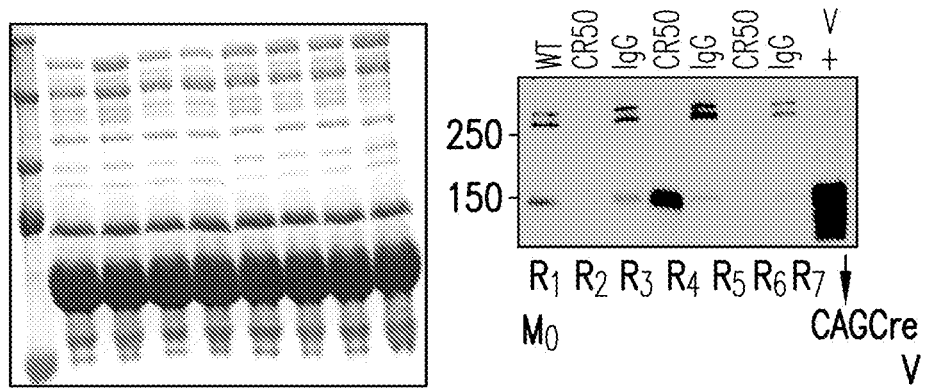
FIG. 10—Shows complete removal of Reelin from mouse plasma by i.p. injection of the CR50 antibody.
Figure 11:
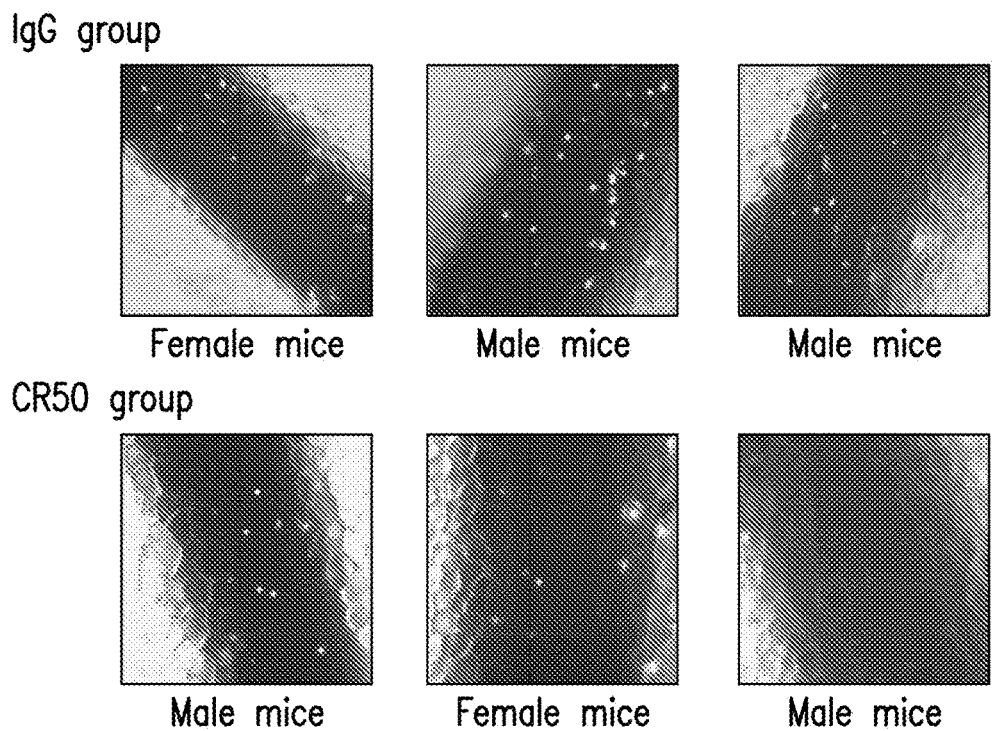
FIG. 11—Shows reduced monocyte adhesion to the vascular endothelium in mice treated with the anti-Reelin CR50 antibody in an in vivo monocyte adhesion assay in CX$_3$CR1w$^{GFP}$ mice. Representative still images are shown.
Figure 12:
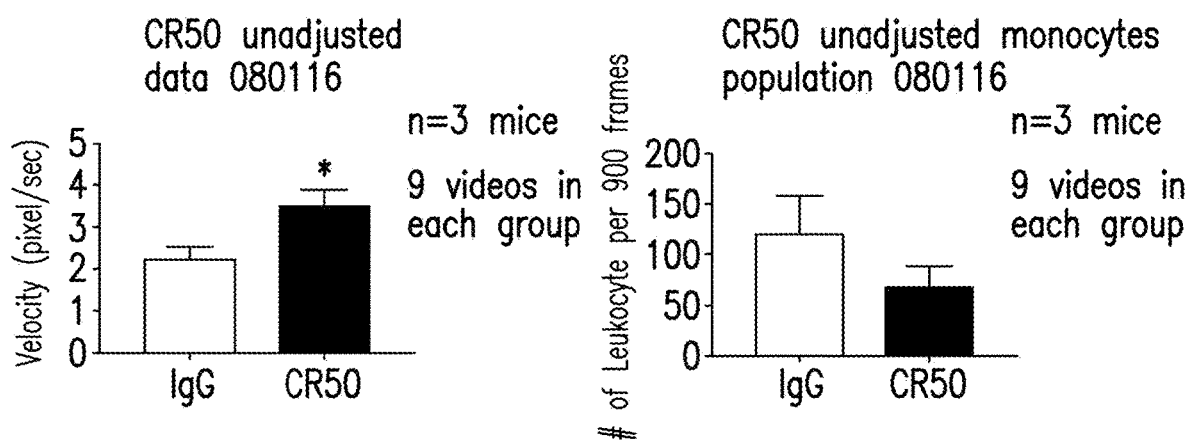
FIG. 12—Shows that treatment with anti-Reelin CR50 antibody blocks leukocyte adhesion to the vascular endothelium in CX$_3$CR1w$^{GFP}$ mice.

It was demonstrated that Reelin can be completely removed from plasma by i.p. injection of the anti-Reelin CR50 antibody (FIG. 10). $CX_3CR1w^{GFP}$ mice treated with the anti-Reelin CR50 antibody exhibited reduced in vivo monocyte adhesion to the vascular endothelium (FIG. 11). FIG. 12 demonstrates reduced in vivo leukocyte adhesion to the vascular endothelium in $CX_3CR1w^{GFP}$ mice treated with CR50 antibody.

Example 16

Role of Reelin in the Signaling

Figure 13:
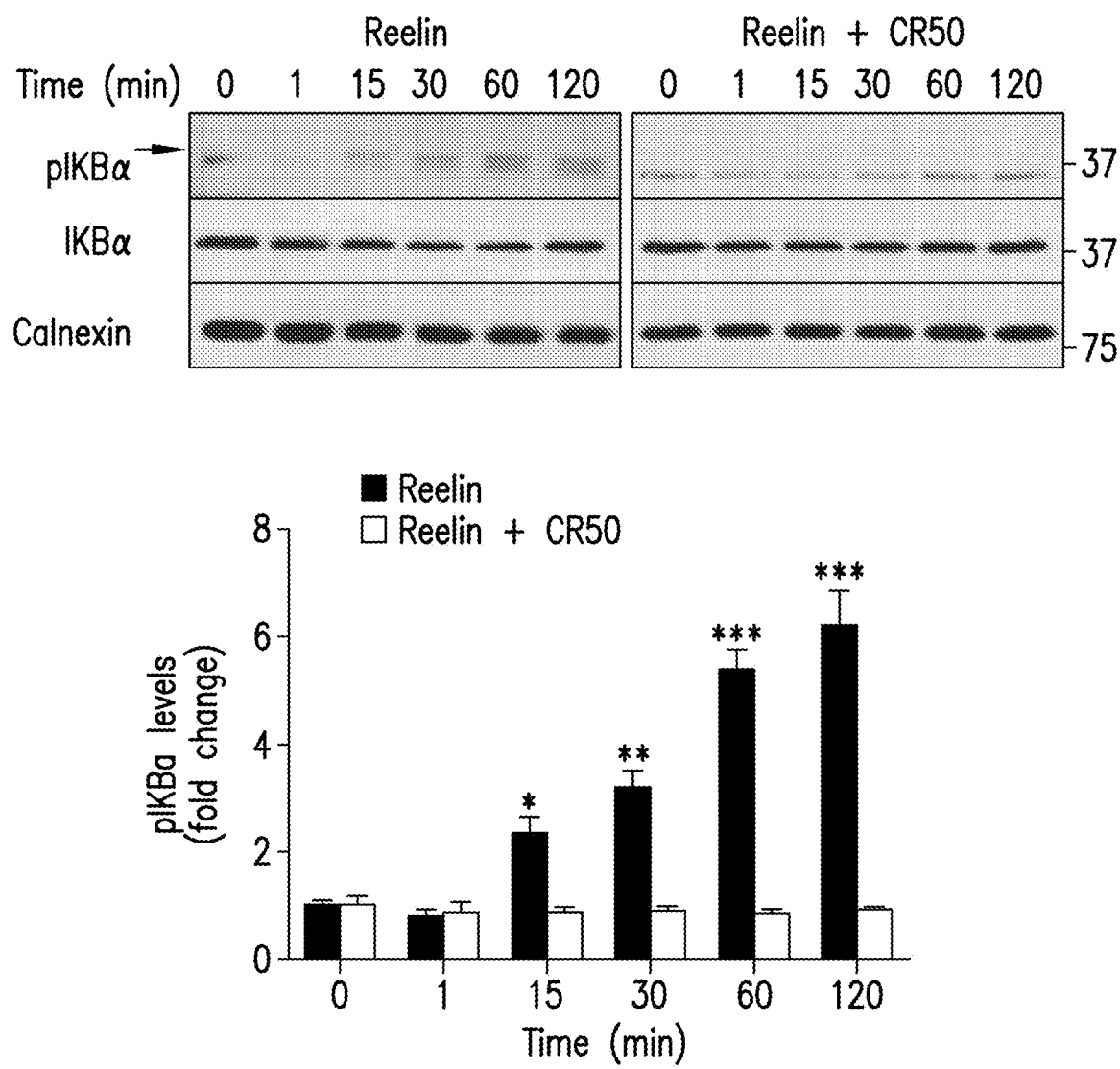
FIG. 13—Shows that Reelin-mediated IKBα activation is blocked by CR50 in HAECs. HAECs were treated with 20 nM Reelin in the presence or absence of 200 nM CR50 for the indicated time points (0, 1, 15, 30, 60 and 120 min). Protein was harvested and subjected to 8% SDS-PAGE gels for pIKBα. IKBα and Calnexin were used as controls. Data were mean±SEM from 3 independent experiments (*, p<0.05;  p<0.01; *, p<0.001).

Further assays were developed using the anti-Reelin CR50 antibody to investigate Reelin-mediated IKBα activation. HAEC's were treated with 20 nM Reelin in the presence or absence of 200 nM CR50. Reelin-mediated IKBα activation was blocked by treatment of HAECs with CR50 (FIG. 13).

Figure 14:
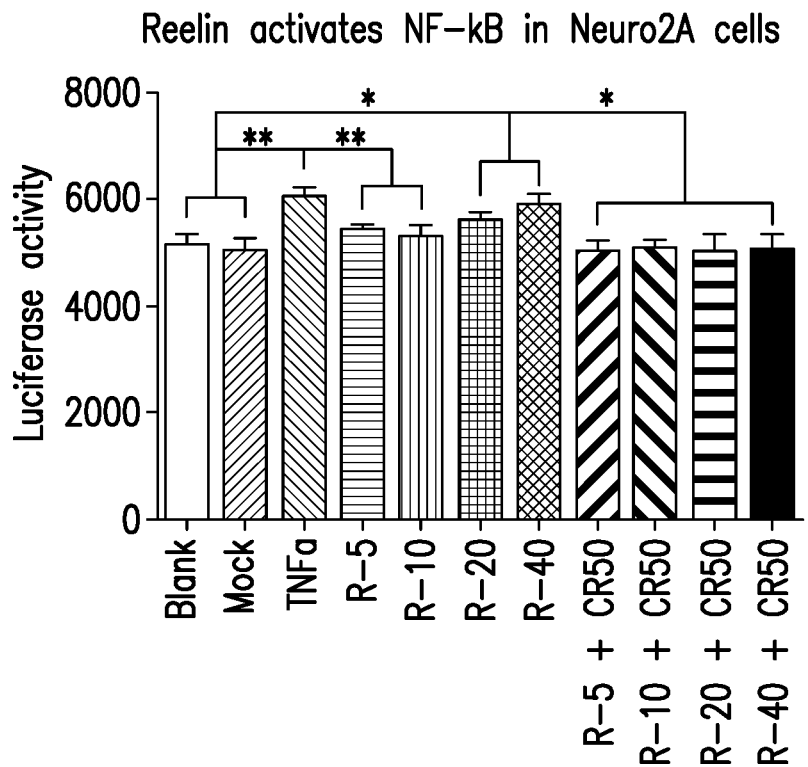
FIG. 14—Shows that Reelin activates NF-κB in Neuro2A cells. Neuro2A cells were transfected with NF-κB-Luc construct for 24 hrs, followed by treatment with Reelin at different concentrations (5, 10, 20 and 40 nM) in the presence or absence of 10-fold CR50 for another 24 hrs. Cells were lysed for luciferase assay. TNFα (1 ng/ml) was used as positive control. Data were mean±SEM from 3 independent experiments (*, p<0.05; **, p<0.01).

Neuro2A cells were transfected with NF-κB-Luc construct followed by treatment with Reelin at different concentrations in the presence or absence of 10-fold CR50. These experiments demonstrated that Reelin activates NF-κB in Neuro2A cells, and that activation is attenuated by treatment with CR50 antibody (FIG. 14).

Figure 15:
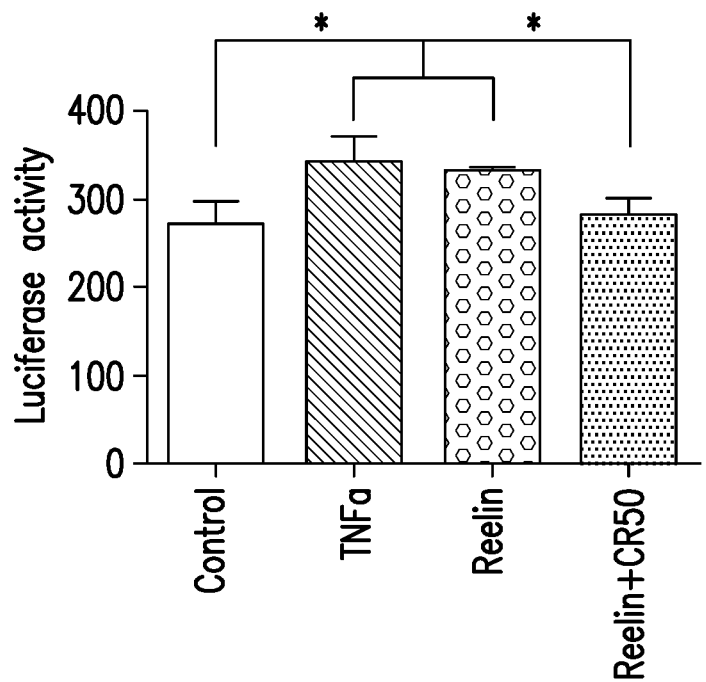
FIG. 15—Shows that Reelin activates NF-κB in HAECs. HAECs were transfected with NF-κB-Luc construct for 24 hrs, followed by treatment with 20 nM Reelin in the presence or absence of 200 nM CR50 for another 24 hrs. Cells were lysed for luciferase assay. TNFα (1 ng/ml) was used as a positive control. Data were mean±SEM from 3 independent experiments. *, p<0.05.

HAECs were transfected with NF-κB-Luc construct followed by treatment with 20 nM Reelin in the presence or absence of 200 nM CR50. Reelin was shown to activate NF-kB in HAECs, and that effect was blocked by treatment with CR50 antibody (FIG. 15).

Figure 16:
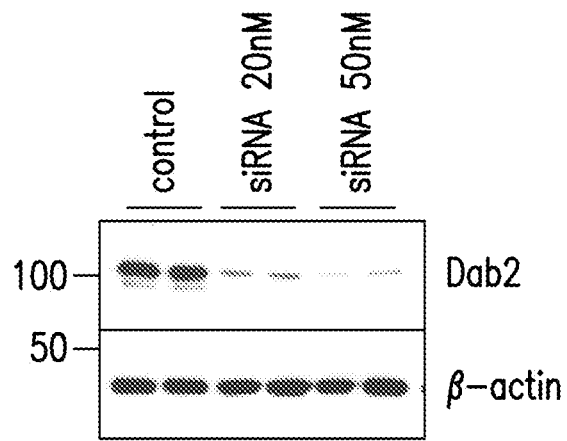
FIG. 16—Shows that endogenous Dab2 was successfully silenced in HAECs by siRNA targeting Dab2. HAECs were transfected with siRNA targeting human Dab2 at different concentrations (20 or 50 nM) on Day 1 and 3. On Day 4, protein was harvested for Western blots.
Figure 17:
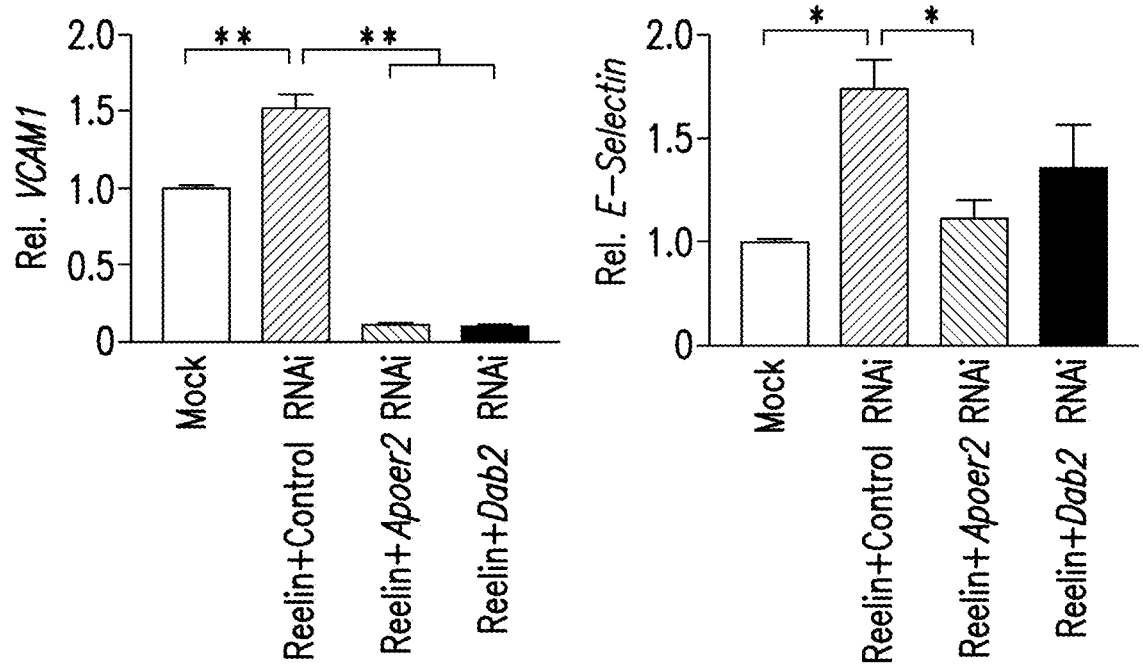
FIG. 17—Shows that Reelin activates the expression of mRNAs for endothelial adhesion molecules in HAECs. Summary plots are shown depicting the relative (Rel.) transcript abundance of VCAM and E-Selectin relative to HPRT1 in HAECs treated with mock or 20 nM Reelin after transfection with 20 nM control (control RNAi) or 20 nM double-stranded RNA targeting either Apoer2 or Dab2 (*, P<0.05; **, P<0.01).

In order to identify the role of Dab2 in Reelin activation, an assay was developed in which endogenous Dab2 was successfully deleted from HAECs using siRNA targeting human Dab2 (FIG. 16). The levels of endothelial adhesion molecules VCAM and E-Selectin relative to HRPT1 were evaluated in HAECs in the presence or absence of Reelin. Reelin was shown to activate the expression of mRNAs for endothelial adhesion molecules in in HAECs (FIG. 17). Treatment of HAECs with double-stranded RNA targeting either Apoer2 or Dab2 significantly reduced VCAM1 and E-Selectin levels compared with cells treated with Reelin and control RNA. This demonstrates that the effect of Reelin is mediated by a signaling cascade that requires Apoer2 and its intracellular adapter protein Dab2 (FIG. 17).

Example 17

Discussion

Besides the nervous system, Reelin is expressed by the liver and present at substantial concentrations in the circulation. In the present work, two distinct types of Reelin conditional knockout mice were employed to determine how Reelin impacts atherosclerosis. Consistent with earlier studies, the results indicate that the circulating pool of Reelin is peripherally-derived, primarily from the liver, and that it does not originate from the CNS. Using these genetic loss-of-function strategies, it was demonstrated that Reelin promotes atherosclerosis in mice.

Atherogenesis is a chronic inflammatory process characterized by the recruitment and transmigration of monocytes into the intima of large vessels and subendothelial accumulation of lipids and lipid-laden foam cells. The studies of Reelin deficiency disclosed herein revealed that the adverse impact of Reelin on atherosclerosis severity entails the enhancement of macrophage accumulation in the atherosclerotic lesions. Prior studies of the Reelin receptors Apoer2 and Vldlr in the context of atherosclerosis investigated cell autonomous mechanisms of these receptors in macrophages, but did not address the role of their cognate ligand, Reelin. Functional analysis of macrophage Apoer2 in $Ldlr^{-/-}$ mice suggested that deficiency of the receptor enhances macrophage susceptibility to lipid accumulation and cell death to augment atherosclerotic plaque progression in vivo. In contrast, the transplantation of Vldlr-expressing macrophages into $Vldlr^{-/-}$ mice markedly accelerated the development of atherosclerotic lesions, suggesting a proatherogenic role of macrophage Vldlr. A study limited to macrophages in culture showed that the activation of Vldlr and Apoer2 by Reelin or ApoE3 induces ABCA1 expression to promote macrophage cholesterol efflux, suggesting a potential antiatherogenic role for Reelin. In another series of experiments the treatment of Vldlr- and Apoer2-overexpressing macrophages with ApoE promoted macrophage conversion from the proinflammatory M1 to the antiinflammatory M2 phenotype, potentially indicating anti-inflammatory actions of the receptors. In contrast to these prior efforts, the present investigation entailing discrete manipulation of Reelin in mice comprehensively addresses how this neurodevelopmentally essential ligand influences atherosclerosis in vivo, and reveals how it aggravates vascular inflammation by enhancing macrophage adhesion and transmigration.

During atherosclerotic lesion development, endothelial dysfunction is an early event, preceding clinical manifestations and complications. After activation by oxidized lipids and proinflammatory cytokines, endothelial cells of the arterial wall express chemokines and adhesion molecules, which provoke leukocyte-endothelial cell adhesion, and in turn the recruitment of inflammatory cells into the lesions. Interestingly, in a prior study neither Vldlr deficiency nor endothelial overexpression of the Vldlr affected atherosclerotic lesion development in Ldlr knockout mice, suggesting that there is modest, if any role for Vldlr in endothelial cells in atherogenesis. On the contrary, it has been previously reported that Apoer2 in endothelial cells reduces NO synthesis and leukocyte-endothelial cell adhesion when Apoer2 is mediating the actions of antiphospholipid antibodies, but enhances NO signaling when ApoE3 is the ligand. The present disclosure demonstrates that hypercholesterolemic $Ldlr^{-/-}$ mice lacking Reelin either systemically or only in their circulation display decreased expression of vascular adhesion markers resulting in attenuated leukocyte-endothelial cell adhesion and reduced atherosclerotic plaque size. Two important differences were observed in the studies in which recombinant adenoviruses were used to delete Reelin selectively in the circulation. First, the total lesion area was much greater in the mice that received recombinant adenovirus (FIG. 4A) than in the tamoxifen experiments (FIG.

3A). This was the case for both, the Ad-Gal control virus and the Ad-Cre virus, compared to the Cre+ and Cre− groups that had received tamoxifen. Second, total plasma cholesterol levels were somewhat higher in the mice that had received Ad-Gal (FIG. 2B), while they were essentially identical in the mice that had received Ad-Cre (FIG. 2B) or tamoxifen (FIG. 1B). These differences likely reflect the contribution of adenovirus-induced inflammation to the results and highlight a possible common complication of using virus-mediated gene transfer or other invasive manipulation (like bone marrow transplantation) in atherosclerosis experiments. Despite these caveats, the results of the adenovirus experiments are consistent with the results obtained in the tamoxifen-treated groups, further supporting the role of Reelin in atherogenesis.

Studies in primary human endothelial cells revealed that direct effects of Reelin on endothelium underlie its pro-inflammatory actions, and that these are likely related to Reelin inhibition of eNOS via Apoer2. Collectively these observations indicate that the negative impact of Reelin on atherosclerosis is at least partially related to its actions on the endothelium.

In summary, the conditional Reelin knockout mouse of the instant disclosure provides a new model to study the impact of Reelin on atherosclerosis and the underlying cellular processes. The cumulative results of the instant disclosure demonstrate for the first time that circulating Reelin promotes atherosclerosis development, and that this is likely attributed to a variety of synergistic molecular mechanisms. These include i) the Reelin-induced reduction of eNOS activity via Apoer2, resulting in ii) increased leukocyte-endothelial adhesion and iii) monocyte/macrophage accumulation in expanding atherosclerotic lesions. These cellular mechanisms, combined with a direct pro-thrombotic function of Reelin, represent peripheral proatherogenic effects of this essential regulator of brain development, synaptic plasticity, learning and memory. Reelin and its surprising modes of action in the context of atherosclerosis provide novel therapeutic targets to pursue in efforts to combat cardiovascular disease.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method of reducing leukocyte adhesion to the vascular cell wall of a subject comprising providing to the subject an amount of an antibody or antibody fragment effective to decrease the activity of Reelin in the circulation of the subject.

2. The method of claim 1, wherein said decreased activity of Reelin comprises reduction of Reelin protein expression or inhibition of Reelin function in the circulation of a subject.

3. The method of claim 1, wherein the antibody is a monoclonal antibody.

4. The method of claim 1, wherein the antibody is a humanized antibody.

5. The method of claim 1, wherein said antibody or antibody fragment performs a function comprising reducing or inhibiting the function of a Reelin protein.

6. The method of claim 1, further comprising administering an antithrombotic drug.

7. The method of claim 1, wherein said subject is afflicted with or at risk of developing atherosclerosis.

8. The method of claim 1, wherein said subject is afflicted with or at risk of developing multiple sclerosis, arthritis, or psoriasis.

9. The method of claim 7, wherein the antibody is a monoclonal antibody.

10. The method of claim 7, wherein the antibody is a humanized antibody.

11. The method of claim 7, further comprising administering an antithrombotic drug.

12. The method of claim 7, wherein said antibody or antibody fragment performs a function comprising reducing or inhibiting the function of a Reelin protein.

13. The method of claim 8, wherein the antibody is a monoclonal antibody.

14. The method of claim 8, wherein the antibody is a humanized antibody.

15. The method of claim 8, wherein said antibody or antibody fragment performs a function comprising reducing or inhibiting the function of a Reelin protein.

\* \* \* \* \*